(12) United States Patent
Wu

(10) Patent No.: US 8,216,195 B2
(45) Date of Patent: Jul. 10, 2012

(54) DISPENSER CAP FOR EYE-DROP CONTAINER

(76) Inventor: Roger Li-Chung Wu, Claremont, CA (US)

( * ) Notice: Subject to any disclaimer, the term of this patent is extended or adjusted under 35 U.S.C. 154(b) by 259 days.

(21) Appl. No.: 12/460,420

(22) Filed: Jul. 17, 2009

(65) Prior Publication Data

US 2010/0174248 A1 Jul. 8, 2010

Related U.S. Application Data

(60) Provisional application No. 61/204,586, filed on Jan. 7, 2009.

(51) Int. Cl.
*A61H 35/02* (2006.01)
*A61M 35/00* (2006.01)
*B67D 3/00* (2006.01)

(52) U.S. Cl. ......... 604/302; 604/295; 222/563; 215/306

(58) Field of Classification Search .......... 604/294–302; 222/562–563; 215/306
See application file for complete search history.

(56) References Cited

U.S. PATENT DOCUMENTS

| | | | | |
|---|---|---|---|---|
| 1,933,260 A * | 10/1933 | Harkness, Jr. | ................ | 222/512 |
| 3,058,466 A * | 10/1962 | Routsong | ...................... | 604/302 |
| 3,143,255 A * | 8/1964 | Leeds | .......................... | 222/479 |
| 3,165,243 A * | 1/1965 | Haynes | .......................... | 222/498 |
| 3,307,752 A * | 3/1967 | Anderson | .................. | 222/465.1 |
| 3,598,121 A * | 8/1971 | Lelicoff | ......................... | 604/302 |
| 3,809,300 A * | 5/1974 | Russell | .......................... | 222/545 |
| 3,860,135 A * | 1/1975 | Yung et al. | .................... | 215/213 |
| 3,872,866 A * | 3/1975 | Lelicoff | ......................... | 604/302 |
| 3,934,590 A * | 1/1976 | Campagna et al. | ........... | 604/302 |
| 4,054,221 A * | 10/1977 | Glover | .......................... | 215/235 |
| 4,085,750 A * | 4/1978 | Bosshold | ...................... | 604/302 |
| 4,543,096 A * | 9/1985 | Keene | .......................... | 604/300 |
| 4,915,268 A * | 4/1990 | Lay et al. | ...................... | 222/498 |
| 4,946,452 A * | 8/1990 | Py | .................................. | 604/301 |
| 4,960,407 A * | 10/1990 | Cope | ............................. | 604/300 |
| 4,973,322 A * | 11/1990 | Jewart | .......................... | 604/300 |
| 5,154,711 A * | 10/1992 | Williams | ...................... | 604/301 |
| 5,207,657 A * | 5/1993 | Gibilisco | ....................... | 604/295 |
| 5,221,017 A * | 6/1993 | Cistone et al. | ................ | 215/235 |
| 5,221,027 A * | 6/1993 | Gibilisco | ....................... | 222/420 |
| 5,267,986 A * | 12/1993 | Py | .................................. | 604/294 |
| 5,295,599 A * | 3/1994 | Smith | ........................... | 215/204 |
| 5,398,837 A * | 3/1995 | Degrassi | ...................... | 220/835 |
| 5,607,410 A * | 3/1997 | Branch | ......................... | 604/302 |
| 5,860,387 A * | 1/1999 | Giveen | .......................... | 116/285 |
| 5,902,292 A * | 5/1999 | Feldman | ...................... | 604/295 |
| 6,010,488 A * | 1/2000 | Deas | ............................. | 604/295 |

(Continued)

*Primary Examiner* — Melanie Hand
*Assistant Examiner* — Paula Craig
(74) *Attorney, Agent, or Firm* — Raymond Y. Chan; David and Raymond Patent Firm

(57) ABSTRACT

A dispenser cap for an eye-drop container includes a cap holder, an eyelid-engaging member, and a cap enclosure pivotally extended from the cap holder alongside the eyelid-engaging member. The eyelid-engaging member has topside adapted for contacting with an eyelid of a user to maintain the eyelid in an opened position. The cap enclosure is outwardly folded away from the eyelid-engaging member for exposing the dispensing nozzle and is folded in to engage with the eyelid-engaging member to create a nozzle cavity for enclosing the dispensing nozzle. Therefore, the dispenser cap not only provides a sealing device for enclosing the dispensing nozzle of the eye-drop container but also forms an eyelid retractor for maintaining the eyelid of the user in an opened position and aligning the dispensing nozzle to the eye of the user.

20 Claims, 16 Drawing Sheets

U.S. PATENT DOCUMENTS

| | | | | |
|---|---|---|---|---|
| 6,090,086 | A * | 7/2000 | Bolden | 604/302 |
| 6,371,945 | B1 * | 4/2002 | Sherman | 604/302 |
| 7,325,708 | B2 * | 2/2008 | Barber | 222/420 |
| 7,331,944 | B2 * | 2/2008 | Py et al. | 604/298 |
| 7,678,089 | B2 * | 3/2010 | Py et al. | 604/302 |
| 2006/0157516 | A1 * | 7/2006 | Barber | 222/420 |
| 2006/0173425 | A1 * | 8/2006 | Meierhoefer | 604/300 |
| 2009/0259204 | A1 * | 10/2009 | Galdeti et al. | 604/302 |
| 2010/0286633 | A1 * | 11/2010 | Marx | 604/296 |

\* cited by examiner

DISPENSER CAP FOR EYE-DROP CONTAINER

CROSS REFERENCE TO RELATED APPLICATION

This is a non-provisional application of a provisional application having an application No. 61/204,586 and a filing date of Jan. 7, 2009.

BACKGROUND OF THE PRESENT INVENTION

1. Field of Invention

The present invention relates to an eye-drop container, and more particularly to a dispenser cap for an eye-drop container, wherein the dispenser cap not only is a cap for sealedly covering the dispensing nozzle of the eye-drop container but also functions as an eye drop dispenser that can maintain the eyelid of the user in an opened position to facilitate the alignment of the dispensing nozzle with the eye of the user during the application of the eye-drop medication.

2. Description of Related Arts

Eye drop medication is commonly used for eye disease treatment. Some eye drops are helpful for relieving eye discomfort such as the using of artificial tear to relieve the dryness of the eyes. Using eye drops is by far the most common way of delivering medication to the eye today.

Traditionally, an user has to unscrew the cap, hold the eye drop bottle directly over the user's eye with one hand and open his/her eyelids with the other hand. The user has to use at least one hand in direct contact with the eyelids to hold them opened which could run the risk of introducing bacteria into the eyes of the user. And in cases where eye drops are prescribed to treat either bacterial or viral conjunctivitis, if the bottle is not handled carefully or if the nozzle itself come in contact with the eye; the entire bottle would be contaminated, resulting in prolonged course of the disease and wasting the money spent to purchase the eye drop. Also, the small eye drop bottle is hard to hold, squeeze, and align with the eyes of the user. This is especially true among elderly or patients with tremor or shaky hands. The users have to maintain the eyelids in an opened position while they bring the bottle close to their eyes to instill the medication. It is hard to align the tip of the eye drop bottle with the eye of the user and control blinking while making sure that the nozzle tip of the bottle does not come in direct contact with the eyeball or eyelids so as to prevent contamination of the eye drop bottle and to make sure the medication does not miss the eyeball.

And with the prices of some of the glaucoma and antibiotic medications currently averaging more than one dollar per drop, a drop of medication missing the eyes of the patients means an increase in their monthly medical expenses and possibly a waste of our national health care resources. Also, since just about all eye drop bottles available today require the users to unscrew the caps off first, many users who are on multiple medications have ended up either placing the wrong cap back onto the wrong bottle causing possible cross-contamination, or simply lose some of the caps altogether. How to insert the eye drop properly without touching the bottle to the eyeball or eyelids could easily become a major issue in today's soft economy.

As an eye care professional myself, the applicant has personally witnessed cases where patients either have lost the caps or mistakenly put the wrong caps on different bottles, yet still continued using the medication even though the bottles clearly had been contaminated. Also because there are so many different categories of glaucoma medications on the market these days and each category has different dosing regimen and is represented by different color on the bottle cap, majority of the patients simply remember the medication by its cap color rather than the actual name of the glaucoma medication. So if the caps are not placed correctly back onto its matching medication bottle, these patients would end up using the wrong medication at a wrong frequency causing adverse reactions.

The applicant has also witnessed cases where either patients were too nervous to have anything come closer to their eyes and therefore couldn't get their eyes wide open enough to instill eye drop, or worse yet, the nozzle actually scratched the cornea causing a painful corneal abrasion. There is a common misperception that the eye drop has to land squarely on the eyeball in order to be effective. But the reality is, if the bottle can come from below the patients' line of sight and deliver the medication into the cul-de-sac area or the area behind the lower eye lids, it will still maintain its effectiveness but also relieve much of the nervousness of the users and most likely eliminate most accidental scraping of the eyes.

Several types of eye drop dispensers which is capable of opening the eyelids for instilling the eye drops are available in the current market. The user can purchase the eye drop dispenser as an add-on device to install to their own eye drop bottle so as to help maintaining the eyelids in the opened position and alignment with the eye when instilling the eye drops into the eye. Lots of patients have to take the eye drop several times a day. They need to carry the eye drop bottles with them to work, school, or other places. It is inconvenient to the users to bring both the eye drop bottle and a separate dispenser. The other drawback is the complicated operation of the current add-on eye drop dispensers. The users always have to first open the cap of the bottle, then put the cap aside, and finally install the dispenser onto the neck portion of the bottle. And it is during this installing procedure that the users could easily touch the nozzle accidentally and cause further contamination. Furthermore, how the add-on dispenser was stored after each use without contamination has yet to be focused.

SUMMARY OF THE PRESENT INVENTION

An object of the present invention is to provide an eye-drop container having a dispenser cap, wherein the dispenser cap, which covers and seals the dispensing nozzle of the eye-drop container, not only functions a sealing device as of the conventional cap, but also forms an eye drop dispenser for maintaining the eyelids of the user in an opened position while aligning the dispensing nozzle with the eyes of the user.

Another object of the present invention is to provide a dispenser cap for an eye-drop container, wherein the cap enclosure can be folded out to disengage with the eyelid engaging member as an eyelid retractor such that when the eyelid engaging member is placed in direct contact with the lower eyelid of the user, it can help to maintain the eyelid at the opened position. Once the cap enclosure is folded in to engage with the eyelid engaging member, the dispensing nozzle of the eye-drop container will then be enclosed and kept from being contaminated.

Another object of the present invention is to provide a dispenser cap for an eye-drop container, wherein the cap enclosure can be folded out to form an eyelid-engaging member such that the eyelid-engaging member is adapted to contact directly with the eyelids of the user to maintain the eyelids at the opened position. Once the eyelid engaging member is folded in or "pinched" together, cap enclosure will be recreated and the dispensing nozzle of the eye-drop container will be enclosed to prevent the dispensing nozzle from being contaminated.

Another object of the present invention is to provide a dispenser cap for an eye-drop container, wherein the dispenser cap can be configured as an universal cap for applying to different types and brands of container so as to lower the manufacturing cost of the dispenser cap. In other words, the dispenser cap does not require altering the original structural design of the eye-drop container, so as to minimize the manufacturing cost of the eye-drop container incorporating with the dispenser cap.

Another object of the present invention is to provide a dispenser cap for an eye-drop container, wherein a user can take the eye drops easily by opening the cap enclosure and maintaining the eyelid at the opened position via the eyelid-engaging member so as to align the dispensing nozzle with the eye. In other words, no add-on component is required for attachment to the eye-drop container.

Another object of the present invention is to provide a dispenser cap for an eye-drop container with a simple structure so that the dispenser cap can be formed in a one-piece integrated design.

Another object of the present invention is to provide a dispenser cap for an eye-drop container, wherein the tip of the dispensing nozzle is enclosed by a tip holder when the cap enclosure is folded in or "pinched" together to engage with the eyelid engaging member so as to prevent contamination of the fluid in the eye-drop container through the dispensing nozzle.

Another object of the present invention is to provide a dispenser cap for an eye-drop container, which can prevent the hands of the user contacting with the dispensing nozzle.

Another object of the present invention is to provide a dispenser cap for an eye-drop container, wherein no expensive, complicated structure, design or construction is required to employ in the present invention in order to achieve the above mentioned objects. Therefore, the present invention successfully provides an economic and efficient solution for not only enhancing a dispensing operation of the eye-drop container to maintain the eyelid at the opened position and to align the dispensing nozzle with the eye but also providing a sealing configuration of the eye-drop container to prevent the contamination thereof.

Accordingly, in order to accomplish the above objects, the present invention provides a dispenser cap for an eye-drop container having a dispensing nozzle, wherein the dispenser cap comprises a cap holder adapted for securely coupling with the eye-drop container, an eyelid engaging member, and a cap enclosure.

The eyelid-engaging member is upwardly extended from the cap holder, wherein the eyelid-engaging member has topside extended slightly above the tip of the dispensing nozzle of the eye-drop container and adapted for contacting directly with the lower eyelid of a user to maintain the eyelid in an opened position. Therefore, when the eye-drop container is in an inverted position, the eyelid-engaging member can pull down the lower eyelid, maintain the eyelid in the opened position, and facilitate the alignment of dispensing nozzle with the eye of the user while delivering the fluid from the dispenser container and into the eye.

The cap enclosure is upwardly and pivotally extended from the cap holder and alongside the eyelid-engaging member to fold between a dispensing position and a storage position. Accordingly, at the dispensing position, the cap enclosure is outwardly folded away from the eyelid-engaging member to expose the dispensing nozzle. At the storage position, the cap enclosure is folded inward or "pinched" together with the eyelid-engaging member to form a nozzle cavity within the eyelid-engaging member and the cap enclosure to seal the dispensing nozzle.

These and other objectives, features, and advantages of the present invention will become apparent from the following detailed description, the accompanying drawings, and the appended claims.

DETAILED DESCRIPTION OF THE PREFERRED EMBODIMENT

Figure 1:
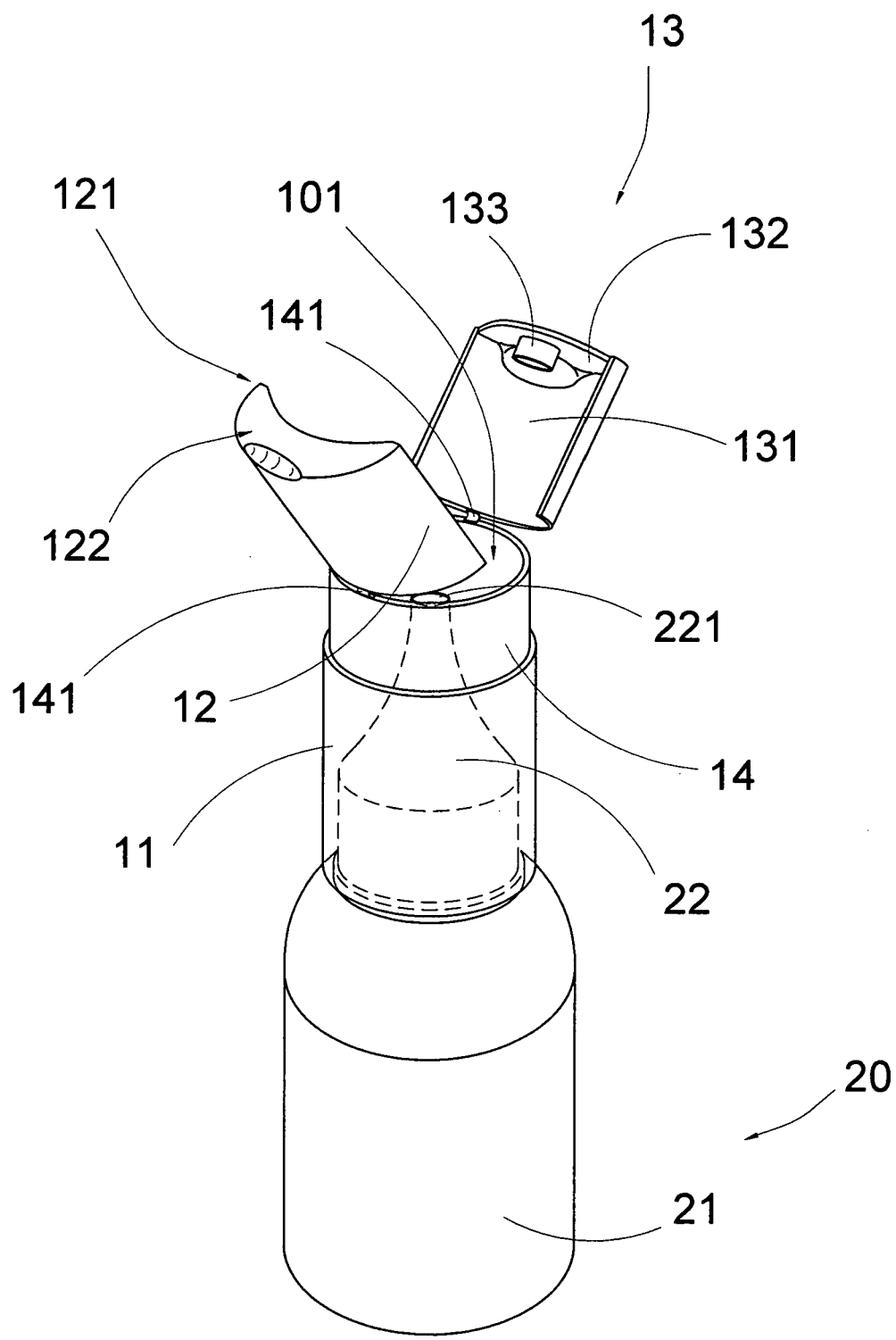
FIG. 1 is a perspective view of a dispenser cap for an eye-drop container according to a preferred embodiment of the present invention.
Figure 2:
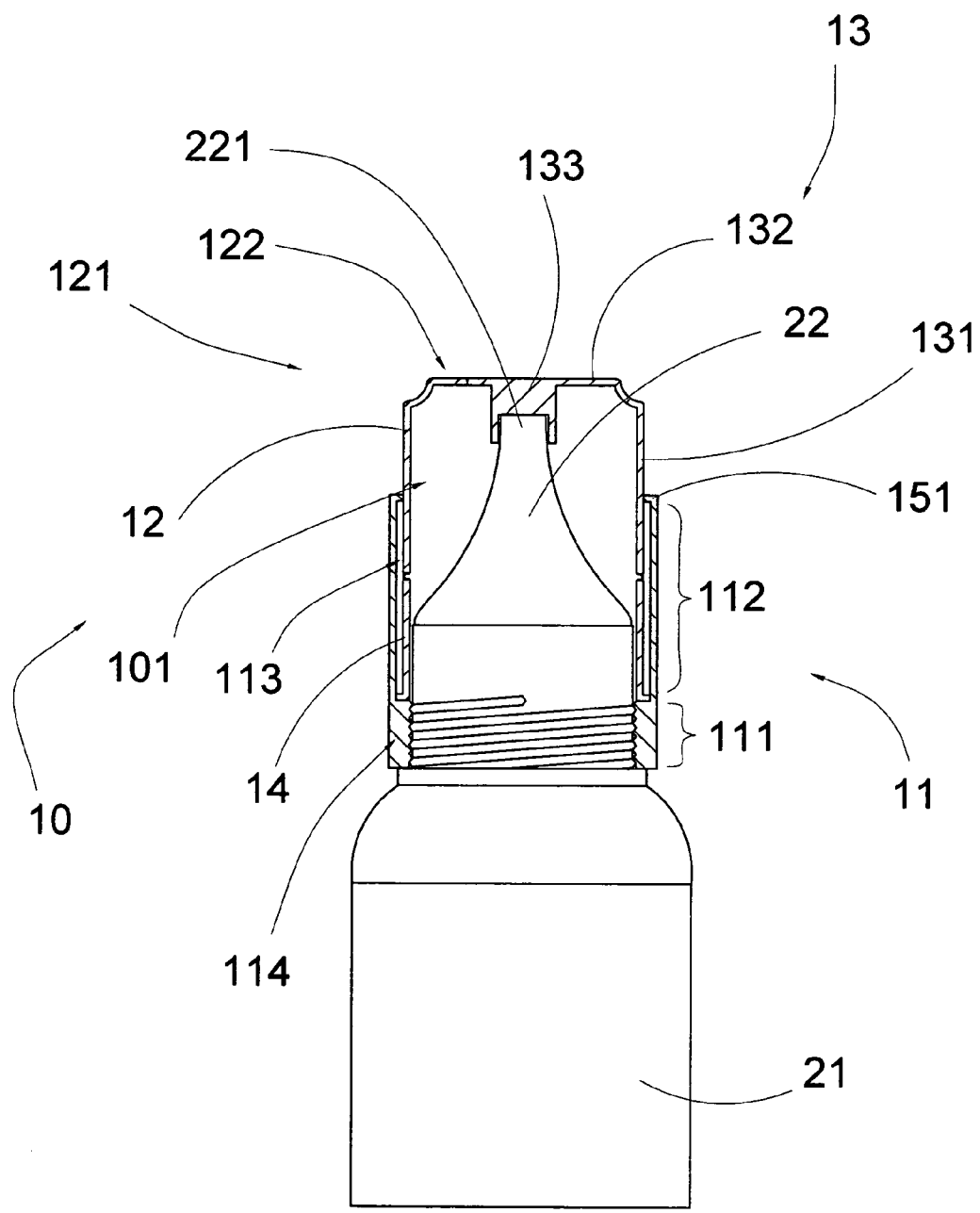
FIG. 2 is a cross-sectional view of the dispenser cap for the eye-drop container according to the above preferred embodiment of the present invention.

Referring to FIGS. 1 and 2 of the drawings, an eye-drop container according to a preferred embodiment of the present invention is illustrated, wherein the eye-drop container comprises a dispenser cap 10 and a dispenser container 20 being closed by the dispenser cap 10.

Figure 6:
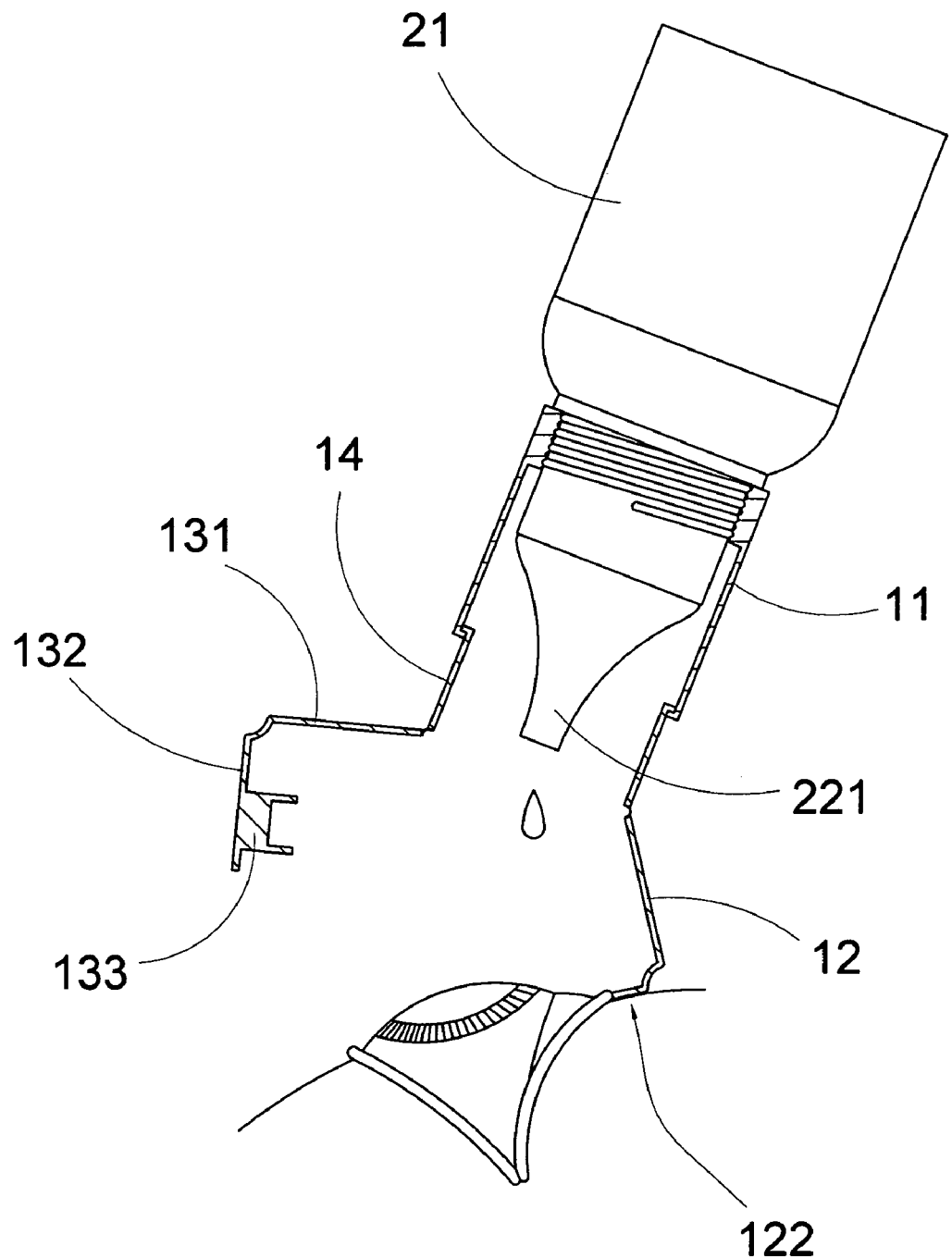
FIG. 6 is a perspective view of the dispenser cap for eye-drop container according to the above preferred embodiment of the present invention, illustrating an eyelid-engaging member contacting with the lower eyelid to maintain the eyelid in an opened position while the dispensing nozzle aligning with an eye of the user.

According to the preferred embodiment, the dispenser container 20 comprises a container body 21 for storing the fluid, such as ophthalmic drops, and a dispensing nozzle 22 upwardly extended from the neck portion of the container body 21 to dispense the fluid when the container body 21 is in an inverted or tilted position. Preferably, the container body 21 is made of squeezable material such that the user is able to squeeze the container body 21 to dispense the drops of the fluid from the tip 221 of the dispensing nozzle 22, as shown in FIG. 6.

The dispenser cap 10 comprises an outer cap holder 11 for detachably engaging with the container body 21, and an enclosure guider coupling with the cap holder 11. The enclosure guider comprises an eyelid-engaging member 12 upwardly and foldably extended from the cap holder 11, and a cap enclosure 13 upwardly and foldably extended from the cap holder 11 at a position alongside the eyelid-engaging member 12.

Accordingly, the eyelid-engaging member 12 is extended upwardly from the cap holder 11 and has one end foldably extended with respect to the cap holder 11 in a pivotally manner, with a top side 121 extended above the tip 221 of the dispensing nozzle 22.

Figure 3:
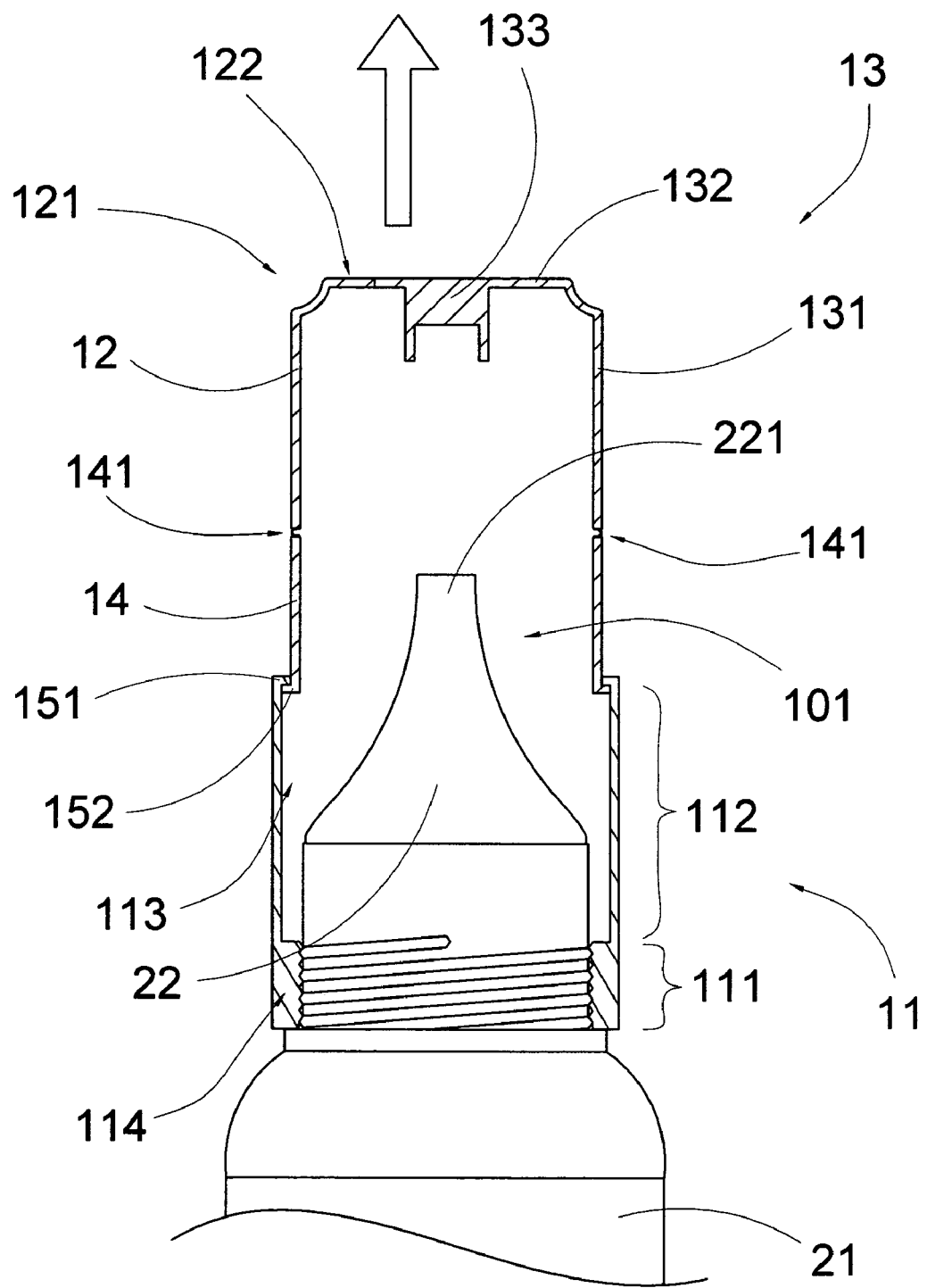
FIG. 3 is an enlarged cross-sectional view of the dispenser cap for the eye-drop container according to the above preferred embodiment of the present invention, illustrating the eyelid-engaging member and the enclosing sidewall being lifted upwardly.
Figure 4:
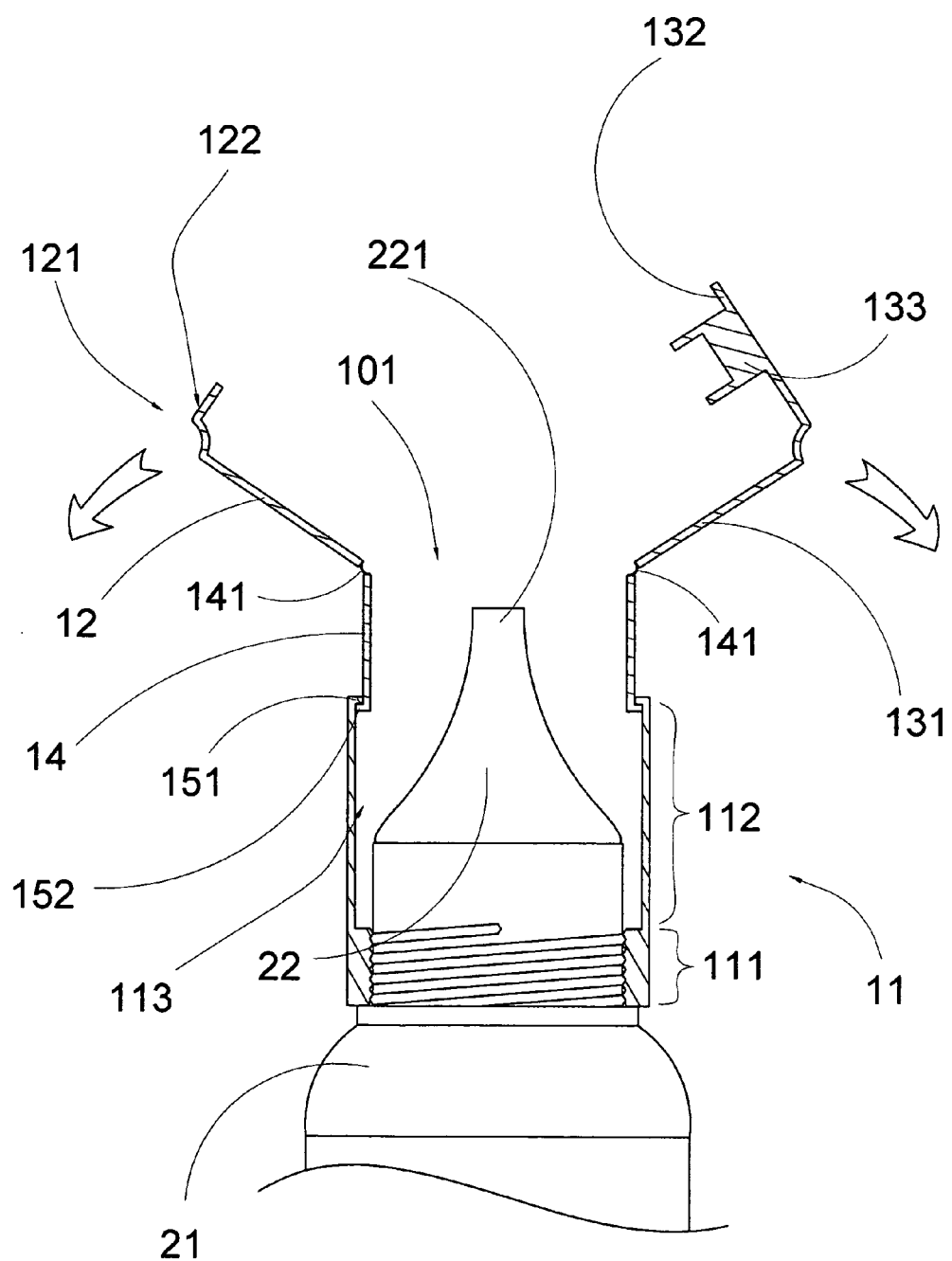
FIG. 4 is a cross-sectional view of the dispenser cap for the eye-drop container according to the above preferred embodiment of the present invention, illustrating the enclosure cap being folded out at the dispensing position.
Figure 5:
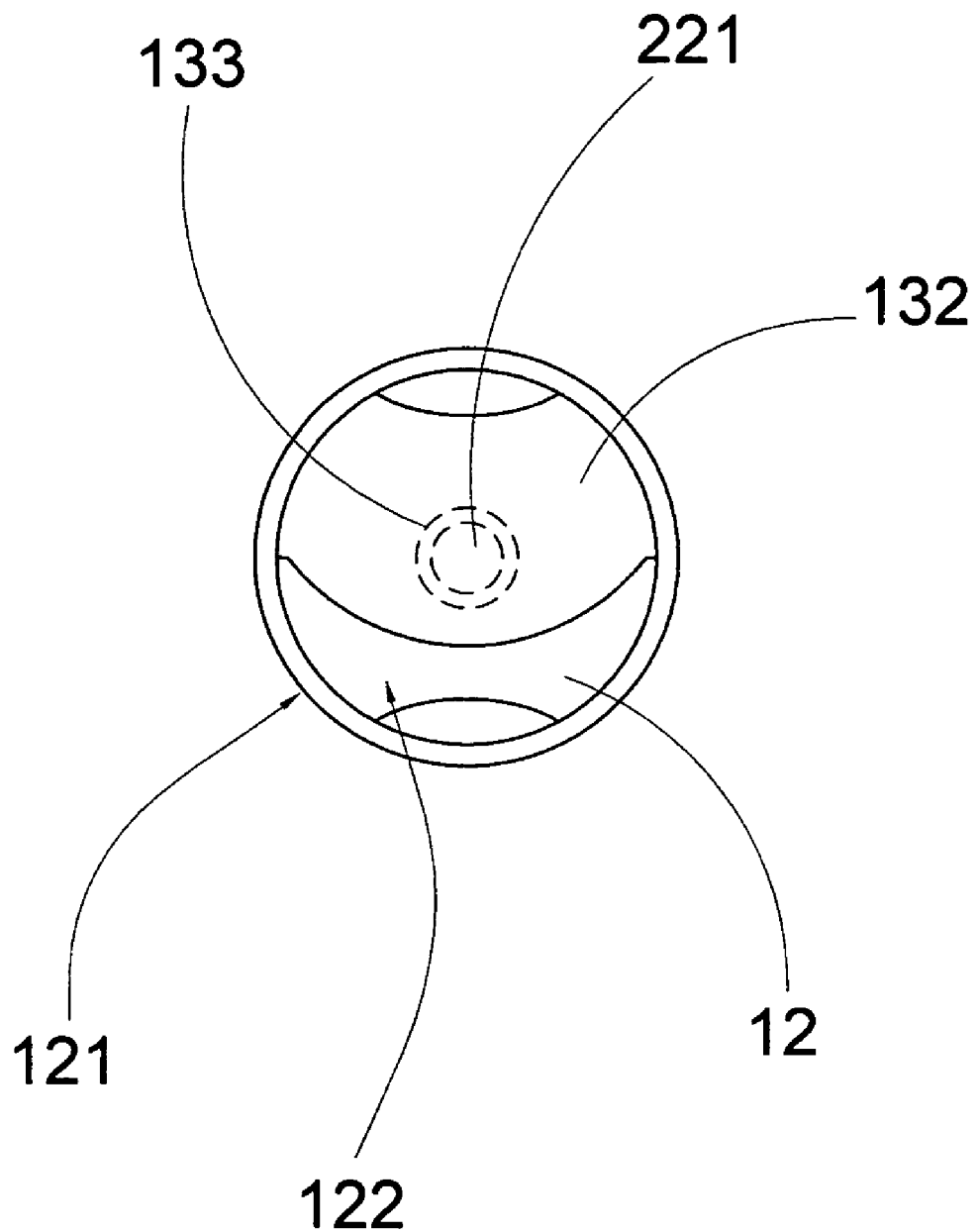
FIG. 5 is a sectional view of the dispenser cap for the eye-drop container according to the above preferred embodiment of the present invention.

As shown in FIGS. 3 and 4, the eyelid-engaging member 12, which is an eyelid retractor having an L-shaped cross section, has an enlarged retracting surface 122 located on the topside with a truncated outer rim. The top retracting surface 122 can have either a smooth surface or a surface with fine grooves, with both a concave inner and a convex outer edge that conform to both the contour of the eyelid and globe of the user. Therefore, the eyelid-engaging member 12 is used as an eyelid opener to maintain the eyelids of the user in an opened position and the truncated edge of the eyelid engaging member will facilitate the alignment of the dispenser container 20 to the eye. In order words, the eyelid-engaging member 12 is coaxially spaced apart from the tip 221 of the dispensing nozzle 22 and is extended slightly above the tip 221.

The cap enclosure 13 is upwardly extended from the cap holder 11 and foldable with respect to the cap holder 11 to either open up to form a dispensing position or fold in to create a storage position. At the dispensing position, as shown in FIG. 4, the cap enclosure 13 is outwardly folded apart from the eyelid-engaging member 12 to expose the tip 221 of the dispensing nozzle 22; and at the storage position, as shown in FIG. 2, the cap enclosure 13 is folded to engage with the eyelid-engaging member 12, i.e. the cap enclosure 13 is folded close or "pinched together" with the eyelid-engaging member 12, to form a nozzle cavity 101 within the cap enclosure 13 and the eyelid-engaging member 12 for enclosing the dispensing nozzle 22.

Accordingly, once in storage position, the cap enclosure 13 will function similar to a traditional bottle cap to enclose the dispensing nozzle 22, prevent the contamination of the fluid through the dispensing nozzle 22, and retard the deterioration of the fluid.

When the cap enclosure 13 is folded apart at the dispensing position, the eyelid-engaging member 12 will come in contact with the user's eyelid, preferably the lower eyelid of the user. The eyelid-engaging member 12 can help to not only maintain the eye in an opened position by pulling down the lower eyelid before instillation of the eye drop, but also align the tip 221 of the dispensing nozzle 22 with the eye of the user. Therefore, when the eye-drop container is held at the inverted position, the tip 221 will point at the lower part of the eyeball with correct alignment to instill the eye drop medication. And because of this improved alignment of the eye-drop container with the eyeball and the fact that the eye-drop container will approach the eye from below the user's line of sight, wastage of the eye drops can be minimized and user's nervousness can be eased, as shown in FIG. 6.

As shown in FIGS. 1 and 2, the cap enclosure 13 comprises an enclosing sidewall 131, pivotally extended from the cap holder 11 with an enclosing ceiling 132, which transversely extends from the enclosing sidewall 131 at a position slightly above the tip 221 of the dispensing nozzle 22 to form a tight seal at the tip 221 when the cap is in the storage position. The enclosing ceiling has a convex inner edge, which will match the concave inner edge of the eyelid-engaging member 12 perfectly to create a complete enclosure for the nozzle when both the eyelid-engaging member 12 and the cap enclosure 13 are folded inward in the storage position. Therefore, when the cap enclosure 13 is folded in a pivotal manner to engage with the eyelid-engaging member 12, the nozzle cavity 101 will be created within the eyelid-engaging member 12, the enclosing sidewall 131, and the enclosing ceiling 132 of the cap enclosure 13.

Moreover, both the eyelid-engaging member 12 and the enclosing sidewall 131 have a predetermined arc-shapes sidewall based on the size and diameter of the dispenser container 20 that when the enclosing sidewall 131 is folded in to meet with the eyelid-engaging member 12 edge-to-edge, the eyelid-engaging member 12 and the enclosing sidewall 131 will form a complete tubular structure enclosing the dispensing nozzle 22. In other words, the two vertical side edges of the eyelid-engaging member 12 will engaged with the two vertical side edges of the enclosing sidewall 131 respectively resulting in a sealed tubular nozzle cavity 101

In addition, when the cap enclosure 13 is pivotally folded in to engage with the eyelid-engaging member 12, the tip 221 of the dispensing nozzle 22 is positioned directly below the enclosing ceiling 132. It is worth mentioning that the enclosing ceiling 132 has a corresponding convex edge fittingly matches the concave inner edge at the top side 121 of the eyelid-engaging member 12 to form the ceiling cover of the dispenser cap 10, as shown in FIG. 2.

The enclosure guider further comprises a guiding member 14 slidably engaged with the cap holder 11 to slide both the eyelid-engaging member 12 and the cap enclosure 13 between the dispensing position and the storage position. Accordingly, the guiding member 14 can be coaxially coupled either on the inside or the outside of the cap holder 11, wherein the guiding member 14 is slid upwardly to guide both the eyelid-engaging member 12 and the cap enclosure 13 into the dispensing position and is slid downward to return to the storage position. In particularly, when the guiding member 14 is upwardly slid with respect to the cap holder 11, both the eyelid-engaging member 12 and the cap enclosure 13 will be lifted and folded open to expose the dispensing nozzle 22; and when the guiding member 14 is slid downward with respect to the cap holder 11, both the eyelid-engaging member 12 and the cap enclosure 13 will simultaneously dropped down and inwardly folded to enclose the dispensing nozzle 22.

As shown in FIGS. 2 to 4, both the eyelid-engaging member 12 and the cap enclosure 13 are upwardly and foldably extended from the guiding member 14 via two resilient joints 141, wherein when the guiding member 14 is upwardly lifted, the eyelid-engaging member 12 and the cap enclosure 13 are outwardly folded at the resilient joints 141 respectively, as shown in FIG. 4. Accordingly, both resilient joints 141, which are made of flexible or elastic material, will have a curved structure to define two resilient ends that not only match the curvatures of the bottle cap, but also connect both the eyelid-engaging member 12 and the cap enclosure 13 to the guiding member 14. One of the resilient joints 141 is integrated between the eyelid-engaging member 12 and the guiding member 14 while the other resilient joint 141 is integrated between the cap enclosure 13 and the guiding member 14. Therefore, because of the flexible characteristic of those two joints, both the eyelid-engaging member 12 and the cap enclosure 13 can be outwardly folded to expose the dispensing nozzle 22 while in the dispensing position.

Furthermore, as shown in FIGS. 1 and 2, the cap enclosure 13 has a tip holder 133 extended from the under side of the cap enclosure's top 132. As shown in FIG. 2, the tip holder 133 has a size and shape matching the tip 221 of the dispensing nozzle 22, so that when the cap enclosure 13 and the eyelid-engaging member 12 are folded together in the storage position, the tip 221 of the dispensing nozzle 22 will be enclosed or sealed by the tip holder 133 of the cap enclosure 13 to prevent accidental spillage or contamination of the fluid.

Accordingly, the tip holder 133 can also act as an additional locking device to secure the cap enclosure 13 in the storage position when the tip 221 of the dispensing nozzle 22 is engaged with the tip holder 133. In other words, the tip holder 133 not only provides protection for the tip 221 of the dispensing nozzle 22 in the storage position but also forms a retentive ring to secure the enclosure cap 13 in the storage position. It's a feature with dual purposes, both preventive and retentive.

As shown in FIGS. 2 to 4, the cap holder 11 has a lower ring portion 111 and an upper ring portion 112, which has an inner diameter slightly larger than the inner diameter of the lower ring portion 111 to create a sliding cavity 113 within the upper ring portion 111. And it is within this small sliding cavity that the guiding member 14 can travel vertically between the storage position and the dispensing position.

As shown in FIGS. 2 and 3, the height of the guiding member 14 is shorter than the height of the sliding cavity 113. When the guiding member 14 is downwardly slid towards the lower ring portion 111 of the cap holder 11, the bottom portions of the eyelid-engaging member 12 and the cap enclosure 13 travel downward within the sliding cavity 113 to ensure the nozzle cavity 101 is tightly created. When the guiding member 14 is upwardly slid, the bottom portions of the eyelid-engaging member 12, the cap enclosure 13, and along with both resilient joints 141, slide out of the sliding cavity 113 to engage in dispensing position. Therefore, the eyelid-engaging member 12 and the cap enclosure 13 can be outwardly folded to expose the dispensing nozzle 22 once both resilient joints 141 are out of the sliding cavity 113.

In order to guide the sliding movement of the guiding member 14, the dispenser cap 10 further comprises a first ring 151 radially and inwardly protruded from the top edge of the sliding cavity 113 and a second ring 152 radially and outwardly protruded from the bottom edge of the guiding member 14, as shown in FIG. 3. When the guiding member 14 is lifted up, the second ring 152 slides upwardly until it reaches the first ring 151 which blocks any further upward sliding movement of the guiding member 14. When the guiding member 14 is pushed down, the second ring 152 slides downwardly until it is stopped by the bottom edge of the sliding cavity 114 to ensure that the bottom portions of both eyelid-engaging member 12 and the cap enclosure 13 are received within the sliding cavity 114. In other words, the distance between the first ring 151 and the bottom edge of the guiding member 14 is the vertical distance permitted for the dispenser cap 10 to travel between dispensing position and storage position.

The cap holder 11 further has an inner threaded portion 114 embedded on the inner side of the lower ring portion 111 of the cap holder 11 for detachably engaging with a neck portion of the eye-drop container. Accordingly, the inner threaded portion 114 of the cap holder 11 is made to match the outer threaded portion of the container body 21 so it can be installed or "screwed" onto the container body 21 at the neck portion. Therefore, the dispenser cap 10 can be incorporated with any existing eye-drop container currently on the market to provide an eyelid-engaging member 12 and a nozzle-enclosing device in one single structure.

Figure 7:
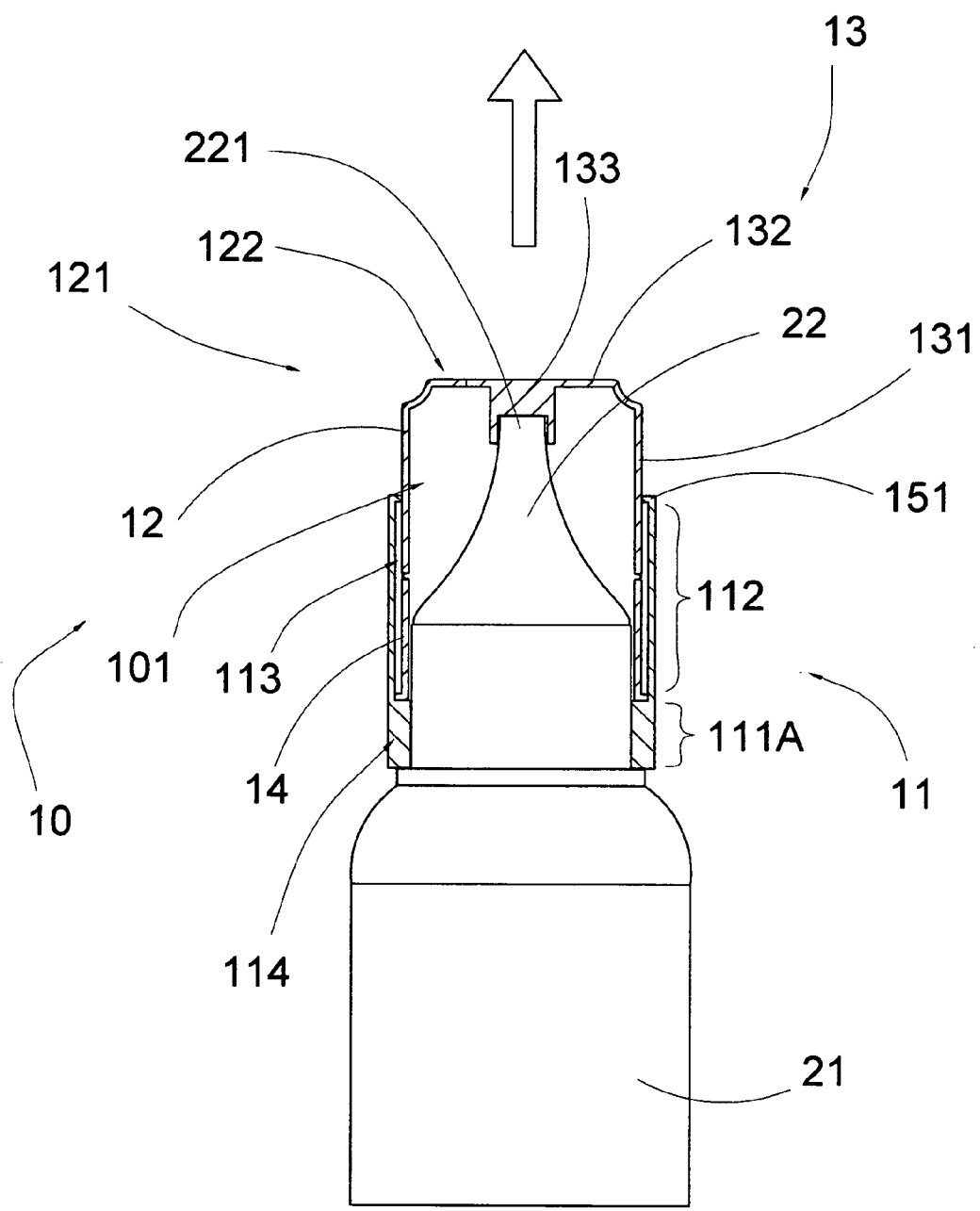
FIG. 7 illustrates an alternative mode of the dispenser cap according to the above preferred embodiment of the present invention.

Alternatively, the lower ring portion 111' of the cap holder 11 can also be permanently affixed to the neck portion of the dispenser container 20, as shown in FIG. 7. Therefore, the manufacturer can choose to permanently seal the cap holder 11 with the dispenser container 20 to prevent the dispenser cap 10 from being lost or reused by the user if it so desires.

According to the preferred embodiment, in order to instill the fluid to the eye of the user, the user simply needs to apply an upward pulling force at the eyelid-engaging member 12 and the cap enclosure 13 to lift up the guiding member 14, wherein the tip holder 133 will disengage with the tip 221 of the dispensing nozzle 22, as shown in FIG. 3. Once the bottom portions of eyelid-engaging member 12 and the cap enclosure 13 are slid out of the sliding cavity 113, the eyelid-engaging member 12 and the cap enclosure 13 will fold apart or "spring open" at the resilient joints 141 respectively to expose the dispensing nozzle 22, as shown in FIG. 4.

It is worth mentioning that the top side of the eyelid-engaging member 12 is further lifted upward to create a clearance between the tip 221 of the dispensing nozzle 22 and the top side of the eyelid-engaging member 12. At its dispensing position, as shown in FIG. 6, the user places the container body 21 at the inverted position and uses the top side 121 of the eyelid-engaging member 12 to pull down the lower eyelid so as to maintain the eyelid at the opened position. Accordingly, the tip 221 of the dispensing nozzle 22 will then align with the eye of the user so that when the user applies a squeezing force at the container body 21, a drop of fluid will flow through the tip 221 of the dispensing nozzle 22 and falls into the cul-de-sac or lower part of the eyeball.

Once the dispensing operation is completed, the user can then pivotally fold the cap enclosure 13 in to engage with the eyelid-engaging member 12 and simultaneously push both the eyelid-engaging member 12 and the cap enclosure 13 back down into the sliding cavity 113 until the tip holder 133 lock in place with the tip 221 of the dispensing nozzle 22.

It is worth mentioning that the dispensing cap 10 not only serves as a sealing device like a conventional cap to enclose the dispensing nozzle 22 at the storage position but also forms an eyelid retractor to maintain the eyelid of the user in an opened position and to help aligning the dispensing nozzle 22 to the eye of the user. Through the engaging structure at the bottom of the cap holder 11, the dispenser cap 10 can be an universal cap to apply on any type of container bodies 21 having an outer threaded portion. In other words, the dispenser cap 10 does not require altering the original structural design of the container body 21, so as to minimize the manufacturing cost of the eye-drop container intended to incorporate with the dispenser cap 10. In addition, both the hand and the eye of the user will less likely touch the dispensing nozzle 22 throughout the entire dispensing process and the contamination of the fluid will be minimized as well.

Figure 8:
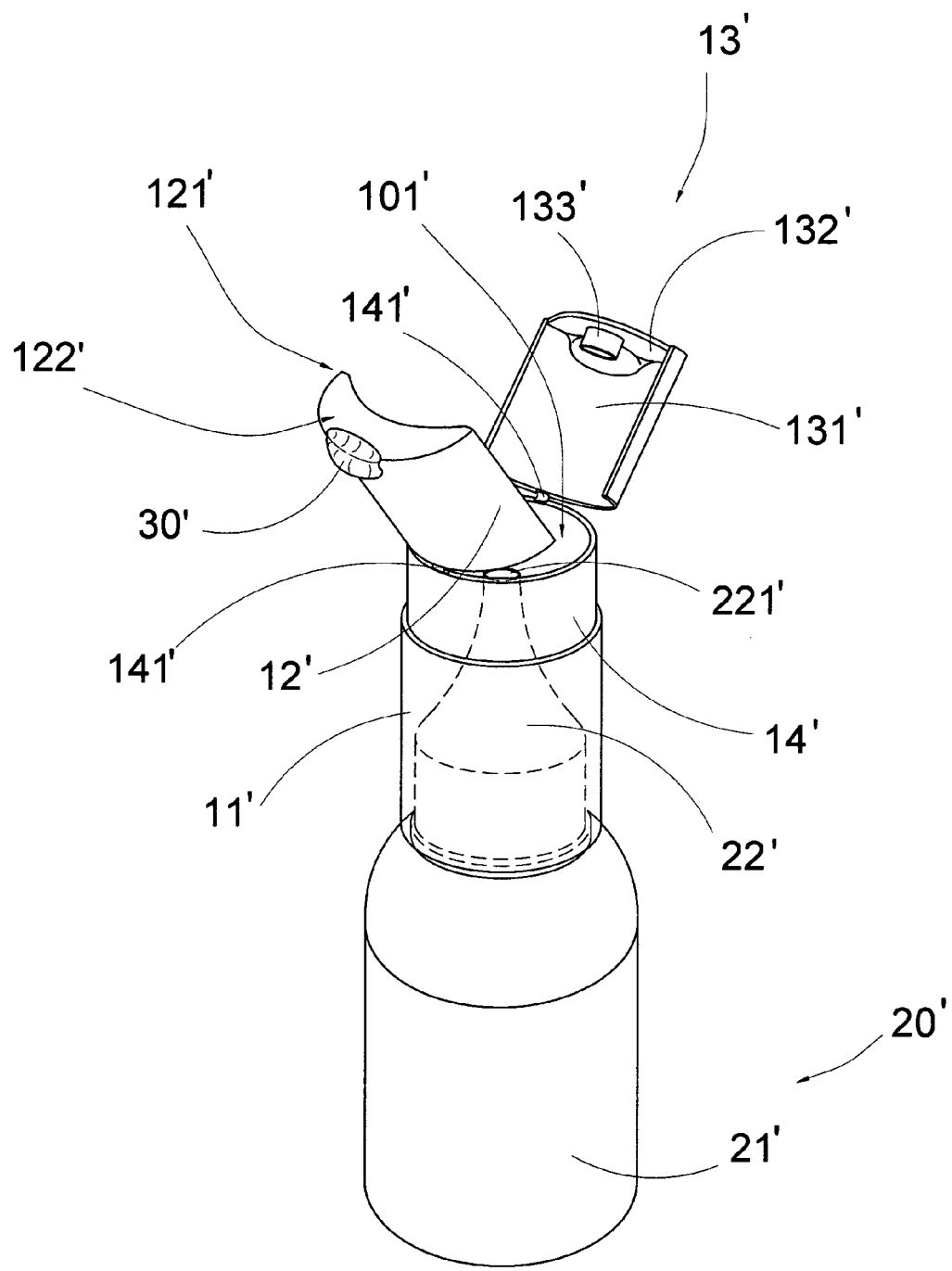
FIG. 8 is a perspective view of a dispenser cap for an eye-drop container according to a second preferred embodiment of the present invention.
Figure 9:
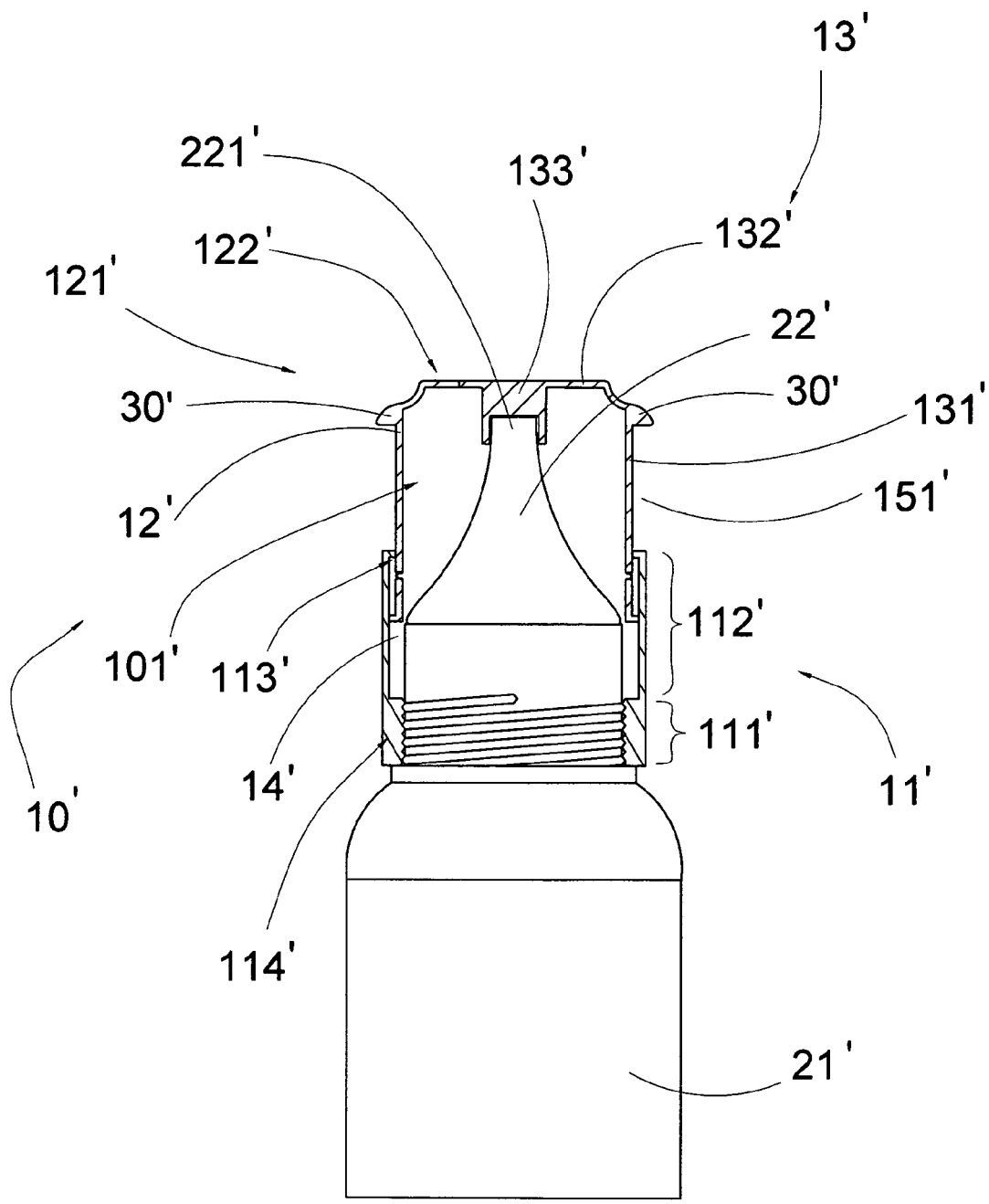
FIG. 9 is a cross-sectional view of the dispenser cap for the eye-drop container according to the above second preferred embodiment of the present invention.

Referring to FIGS. 8 and 9 of the drawings, an eye-drop container of a second preferred embodiment illustrates an alternative mode of the first embodiment of the present invention, wherein the eye-drop container comprises a dispenser cap 10' and a dispenser container 20' being closed by the dispenser cap 10'.

Figure 13:
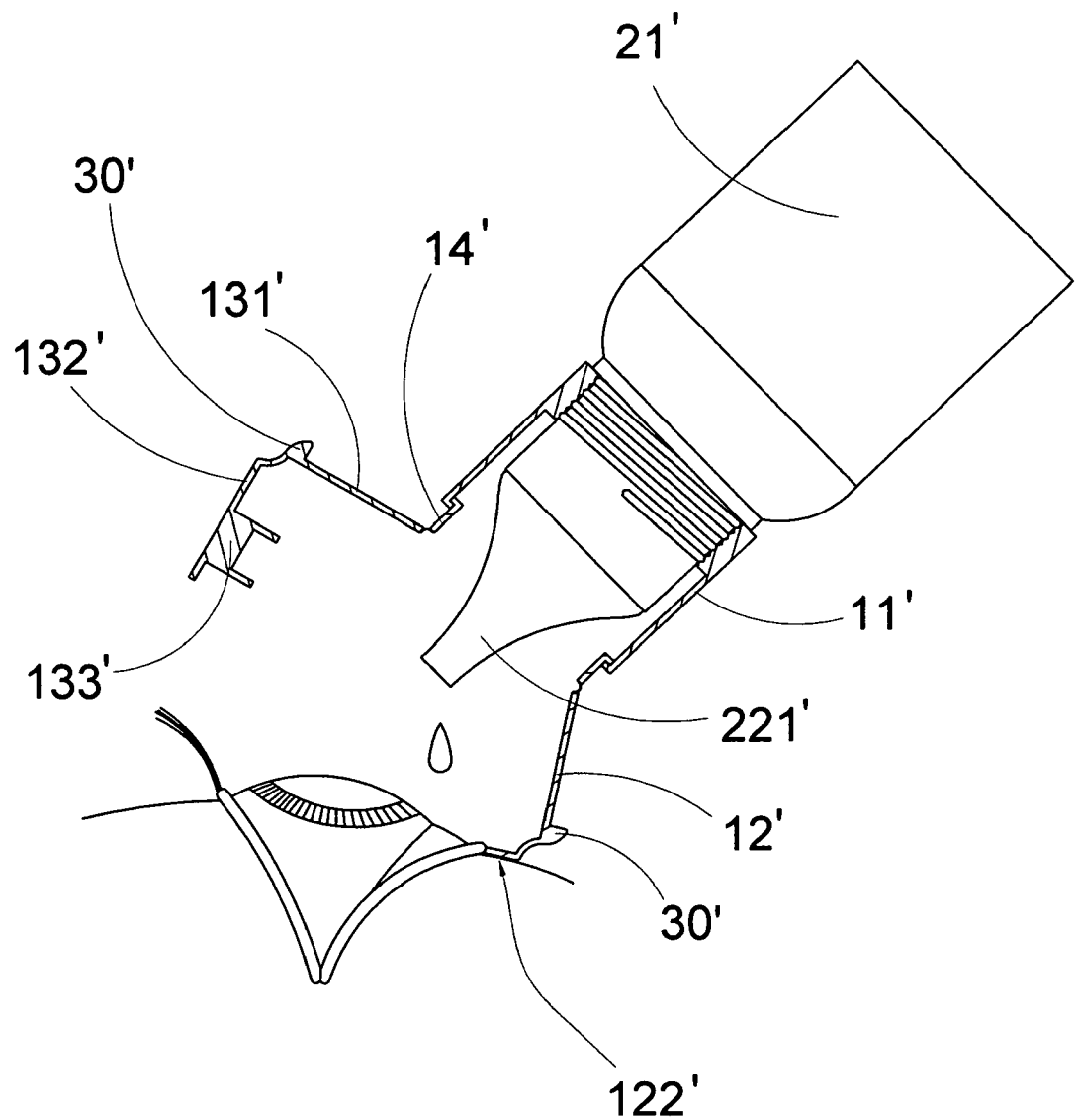
FIG. 13 is a perspective view of the dispenser cap for eye-drop container according to the above second preferred embodiment of the present invention, illustrating an eyelid-engaging member contacting with the lower eyelid to maintain the eyelid in an opened position while the dispensing nozzle aligning with an eye of the user.

According to the preferred embodiment, the dispenser container 20' comprises a container body 21' for storing fluid, such as ophthalmic drops, and a dispensing nozzle 22' upwardly extended from the neck portion of the container body 21' to dispense the fluid when the container body 21' is in an inverted or tilted position. Preferably, the container body 21' is made of squeezable material that's readily available currently so that the user will be able to squeeze the container body 21' to dispense the drops, as shown in FIG. 13.

The dispenser cap 10' comprises an outer cap holder 11' for detachably engaging with the container body 21', and an enclosure guider coupling with the cap holder 11'. The enclosure guider comprises an eyelid-engaging member 12' upwardly and foldably extended from the cap holder 11', and a cap enclosure 13' upwardly and foldably extended from the cap holder 11' at a position opposite the eyelid-engaging member 12'.

Accordingly, the eyelid-engaging member 12' is extended upwardly from the cap holder 11' and has one end foldably extended with respect to the cap holder 11' in a pivotal manner, with a top side 121' extended slightly above the tip 221' of the dispensing nozzle 22'.

Figure 10:
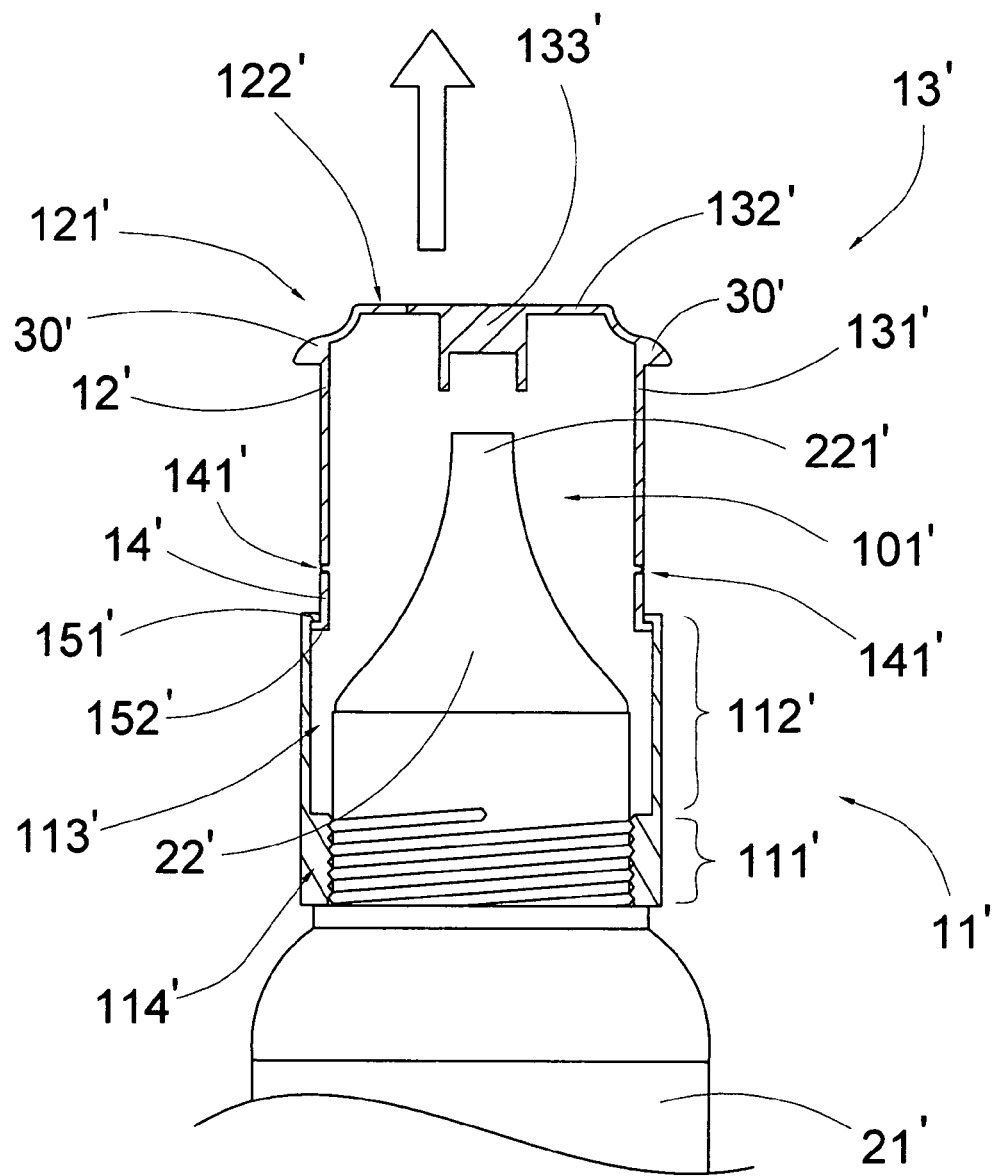
FIG. 10 is an enlarged cross-sectional view of the dispenser cap for the eye-drop container according to the above second preferred embodiment of the present invention, illustrating the eyelid-engaging member and the enclosing sidewall being lifted upwardly.
Figure 11:
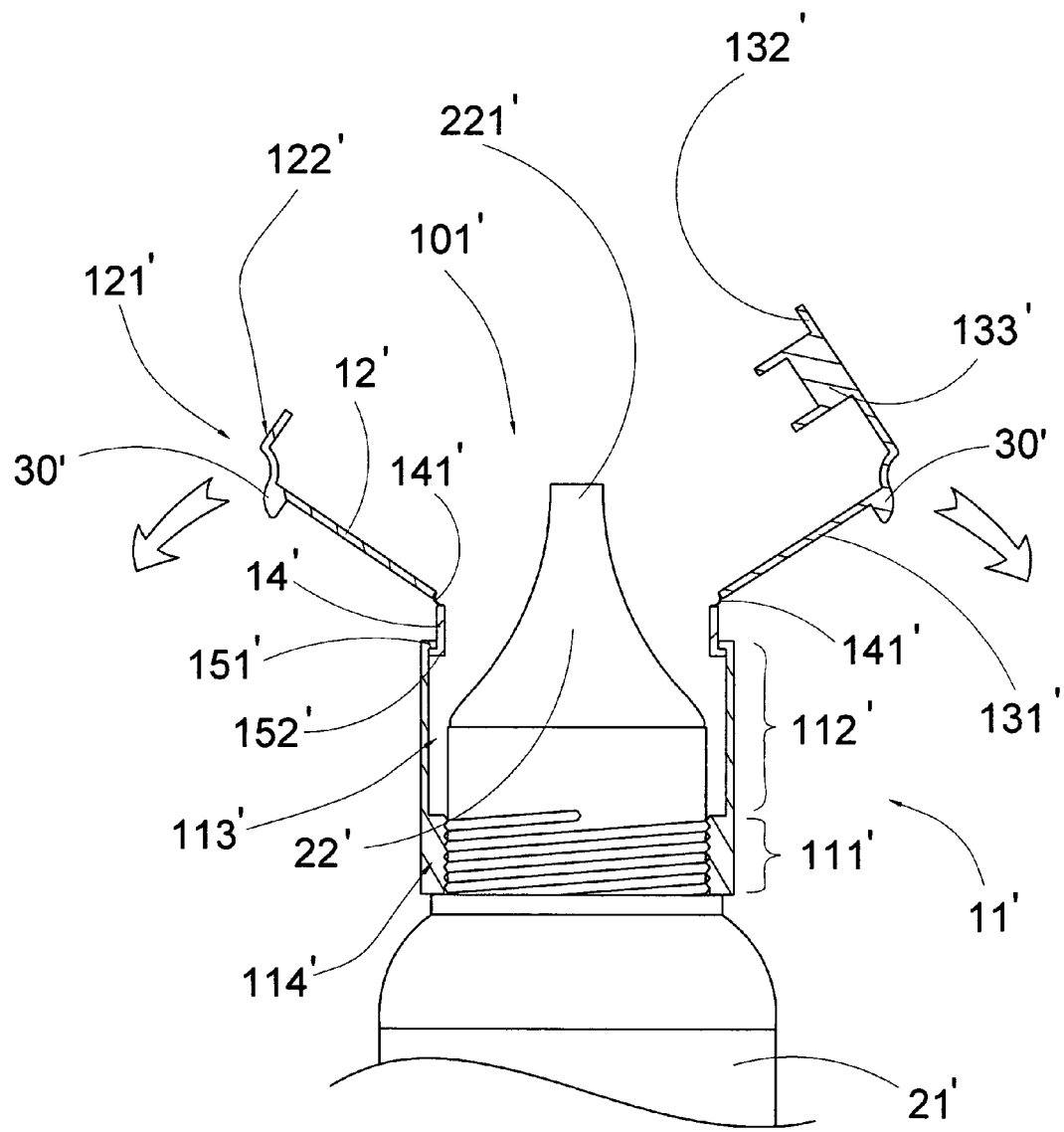
FIG. 11 is a partially cross-sectional view of the dispenser cap for the eye-drop container according to the above second preferred embodiment of the present invention, illustrating the enclosure cap being folded out at a dispensing position.
Figure 12:
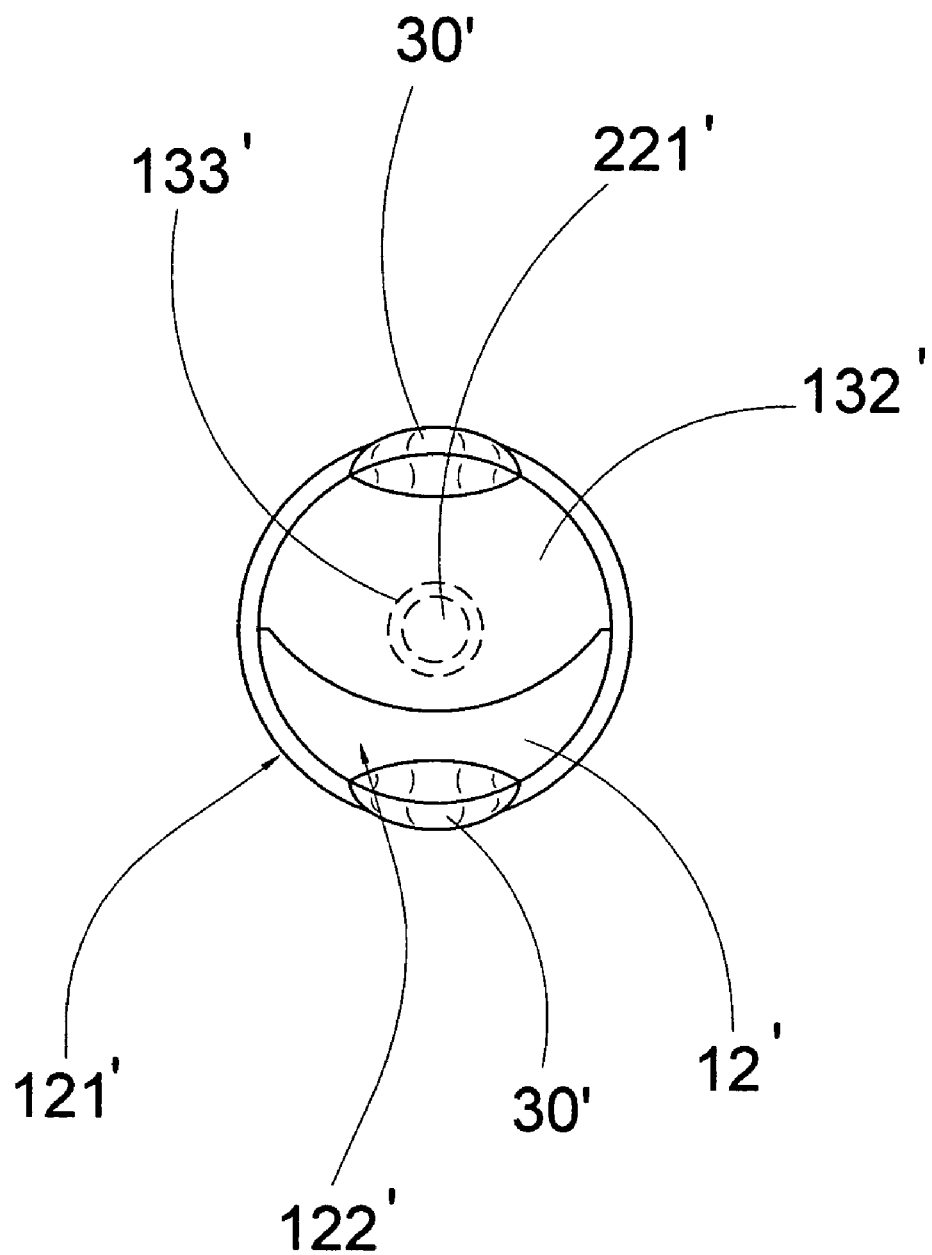
FIG. 12 is a top sectional view of the dispenser cap for the eye-drop container according to the above second preferred embodiment of the present invention.

As shown in FIGS. 10 and 11, the eyelid-engaging member 12', having an L-shaped cross section, will have an enlarged engaging surface 122' located on the top side and a truncated outer rim '. The top engaging surface 122' can be either a smooth surface or a surface with fine grooves, with both a concave inner edge and a convex outer edge that conform to the contour of the eyelid and globe of the user. Therefore, the eyelid-engaging member 12' is used as an eyelid opener or an eyelid retractor to maintain the eyelids of the user in an opened position and the truncated edge of the eyelid-engaging member 12' will facilitate the alignment of the bottle to the eye. In order words, the eyelid-engaging member 12' is coaxially spaced apart from the tip 221' of the dispensing nozzle 22' and is extended slightly above the tip 221'.

The cap enclosure 13' is upwardly extended from the cap holder 11' and foldably extended with respect to the cap holder 11' to either open up to form a dispensing position or fold close to create a storage position. At the dispensing position, as shown in FIG. 11, the cap enclosure 13' is outwardly folded apart from the eyelid-engaging member 12' to expose the tip 221' of the dispensing nozzle 22'; and at the storage position, as shown in FIG. 9, the cap enclosure 13' is folded close or "pinched together" with the eyelid-engaging member 12' to form a nozzle cavity 101' within the two pieces for enclosing the dispensing nozzle 22'.

Accordingly, once in storage position, the cap enclosure 13' will function similar to a traditional bottle cap to enclose the dispensing nozzle 22', prevent the contamination of the fluid through the dispensing nozzle 22', and retard the deterioration of the fluid.

When the cap enclosure 13' is folded apart at the dispensing position, the eyelid-engaging member 12' will come in contact with the user's lower eyelid. The eyelid-engaging member will help not only maintaining the eye in an opened position by pulling down the lower eyelid before instillation of the eye drop, but also aligning the tip 221' of the dispensing nozzle 22' with the eyes of the user. Therefore, when the eye-drop container is held at the inverted position, the tip 221' will point at the lower part of the eyeball with correct alignment to instill the eye drop. And because of this improved alignment of the bottle with the eyeball and the fact that the bottle will approach the eye from below the user's line of sight, wastage of the eye drops can be minimized and user's nervousness can be eased, as shown in FIG. 13.

As shown in FIGS. 8 and 9, the cap enclosure 13' comprises an enclosing sidewall 131', pivotally extended from the cap holder 11' with an enclosing ceiling 132', which transversely extends from the enclosing sidewall 131' at a position slightly above the tip 221' of the dispensing nozzle 22' to form a tight seal at the tip 221' when the cap is in the storage position. The enclosing ceiling 132' has a convex inner edge which will match with the concave inner edge of the eyelid-engaging member 12' perfectly to create a complete enclosure for the nozzle when both the eyelid-engaging member 12' and the cap enclosure 13' are folded inward in the storage position. Therefore, when the cap enclosure 13' is folded in a pivotal manner to engage with the eyelid-engaging member 12', the nozzle cavity 101' is created within the eyelid-engaging member 12', the enclosing sidewall 131', and the enclosing ceiling 132' of the cap enclosure 13'.

Moreover, both the eyelid-engaging member 12' and the enclosing sidewall 131' have a predetermined arc-shape sidewall based on the size and diameter of the bottle that when the enclosing sidewall 131' is folded in to meet with the eyelid-engaging member 12' edge-to-edge, they will form a complete tubular structure to enclose the dispensing nozzle 22'. In other words, the two vertical side edges of the eyelid-engaging member 12' will engaged with the two vertical side edges of the enclosing sidewall 131' respectively resulting in a sealed tubular nozzle cavity 101'.

The enclosure guider further comprises a guiding member 14' slidably engaged with the cap holder 11' to slide both the eyelid-engaging member 12' and the cap enclosure 13' between the dispensing position and the storage position. Accordingly, the guiding member 14' can be coaxially coupled either on the inside or on the outside of the cap holder 11', wherein the guiding member 14' is slid upwardly to guide both the eyelid-engaging member 12' and the cap enclosure 13' into the dispensing position and is slid downward to return to the storage position. In particularly, when the guiding member 14' is upwardly slid with respect to the cap holder 11', both the eyelid-engaging member 12' and the cap enclosure 13' will be lifted and folded open to expose the dispensing nozzle 22'; and when the guiding member 14' is slid downward with respect to the cap holder 11', both the eyelid-engaging member 12' and the cap enclosure 13' will simultaneously dropped down and inwardly folded to enclose the dispensing nozzle 22'.

As shown in FIGS. 9 to 11, both the eyelid-engaging member 12' and the cap enclosure 13' are upwardly and foldably extended from the guiding member 14' via two resilient joints 141', wherein when the guiding member 14' is upwardly lifted, the eyelid-engaging member 12' and the cap enclosure 13' are outwardly folded at the resilient joints 141' respectively, as shown in FIG. 11. Accordingly, both resilient joints 141', which are made of flexible or elastic material, will have a curved structure to define two resilient ends that not only match the curvatures of the bottle cap, but also connect both the eyelid-engaging member 12' and the cap enclosure 13' to the guiding member 14'. One of the resilient joints 141' is integrated between the eyelid-engaging member 12' and the guiding member 14' while the other resilient joint 141' is integrated between the cap enclosure 13' and the guiding member 14'. Therefore, because of the flexible characteristic of those two joints, both the eyelid-engaging member 12' and the cap enclosure 13' can be outwardly folded to expose the dispensing nozzle 22' while in the dispensing position.

Furthermore, as shown in FIGS. 8 and 9, the cap enclosure 13' has a tip holder 133' extended from the under side of the cap enclosure's top 132'. As shown in FIG. 9, the tip holder 133' has a size and shape matching the tip 221' of the dispensing nozzle 22', so that when the cap enclosure 13' and the eyelid-engaging member 12' are folded together in the storage position, the tip 221' of the dispensing nozzle 22' will be enclosed or sealed by the tip holder 133' of the cap enclosure 13' to prevent accidental spillage or contamination of the fluid.

Accordingly, the tip holder 133' can also act as an additional locking device to secure the cap enclosure 13' in the storage position when the tip 221' of the dispensing nozzle 22' is engaged with the tip holder 133'. In other words, the tip holder 133' not only provides protection for the tip 221' of the dispensing nozzle 22' in the storage position but also forms a retentive ring to secure the enclosure cap 13' in the storage position. It's a feature with dual purposes, both preventive and retentive.

As shown in FIGS. 8 to 14, the dispenser cap 10' further comprises two actuating members 30' or "lips" that outwardly protrude from the outer circumferential surfaces of the sidewall of the eyelid-engaging member 12' and the enclosing sidewall 131' of the cap enclosure 13' respectively so that the user can pull up both the eyelid-engaging member 12' and the cap enclosure 13' more easily at the actuating members 30' prior to instillation.

As shown in FIGS. 9 to 11, the cap holder 11' has a lower ring portion 111' and an upper ring portion 112', which has an inner diameter slightly larger than the inner diameter of the lower ring portion 111' to create a sliding cavity 113' within the upper ring portion 112'. And it is within this small sliding cavity that the guiding member 14' can travel vertically between the storage position and the dispensing position.

As shown in FIGS. 9 and 10, the height of the guiding member 14' should be shorter than the height of the sliding cavity 113'. When the guiding member 14' is downwardly slid towards the lower ring portion 111' of the cap holder 11', the bottom portions of the eyelid-engaging member 12' and the cap enclosure 13' will travel downward simultaneously within the sliding cavity 113' to ensure the nozzle cavity 101' is tightly created. And reversibly when the guiding member 14' is slid upward, the bottom portions of the eyelid-engaging member 12', the cap enclosure 13', and along with both resilient joints 141', will slide out of the sliding cavity 113' to engage in dispensing position. Therefore, the eyelid-engaging member 12' and the cap enclosure 13' can be outwardly folded to expose the dispensing nozzle 22' once both resilient joints 141' are out of the sliding cavity.

In order to guide the sliding movement of the guiding member 14', the dispenser cap 10' further comprises a first ring 151' radially and inwardly protruded from the top edge of the sliding cavity 114' and a second ring 152' radially and outwardly protruded from the bottom edge of the guiding member 14', as shown in FIG. 10. When the guiding member 14' is lifted up, the second ring 152' will slide upward until it reaches the first ring 151', which serves as a stop that blocks any further upward sliding movement of the guiding member 14'. When the guiding member 14' is pushed down, the second ring 152' will slide downward until it is stopped by the bottom edge of the sliding cavity 114' to ensure that the bottom portions of both eyelid-engaging member 12' and the cap enclosure 13' are received within the sliding cavity 114'. In other words, the distance between the first ring 151' and the bottom edge of the guiding member 14' is the vertical distance permitted for the dispenser cap 10' to travel between dispensing position and storage position.

Furthermore, the cap holder 11' includes an inner threaded portion 114' embedded on the inner side of the lower ring portion 111' of the cap holder 11' for detachably engaging with the neck portion of the eye-drop container. Accordingly, the inner threaded portion 114' of the cap holder 11' will be made to match the outer threaded portion of the container body 21' so it can be installed or "screwed" onto the container body 21' at the neck portion. Therefore, the dispenser cap 10' can be incorporated with any existing eye-drop container currently on the market to provide an eyelid-engaging member and a nozzle enclosing device in one single structure.

Figure 14:
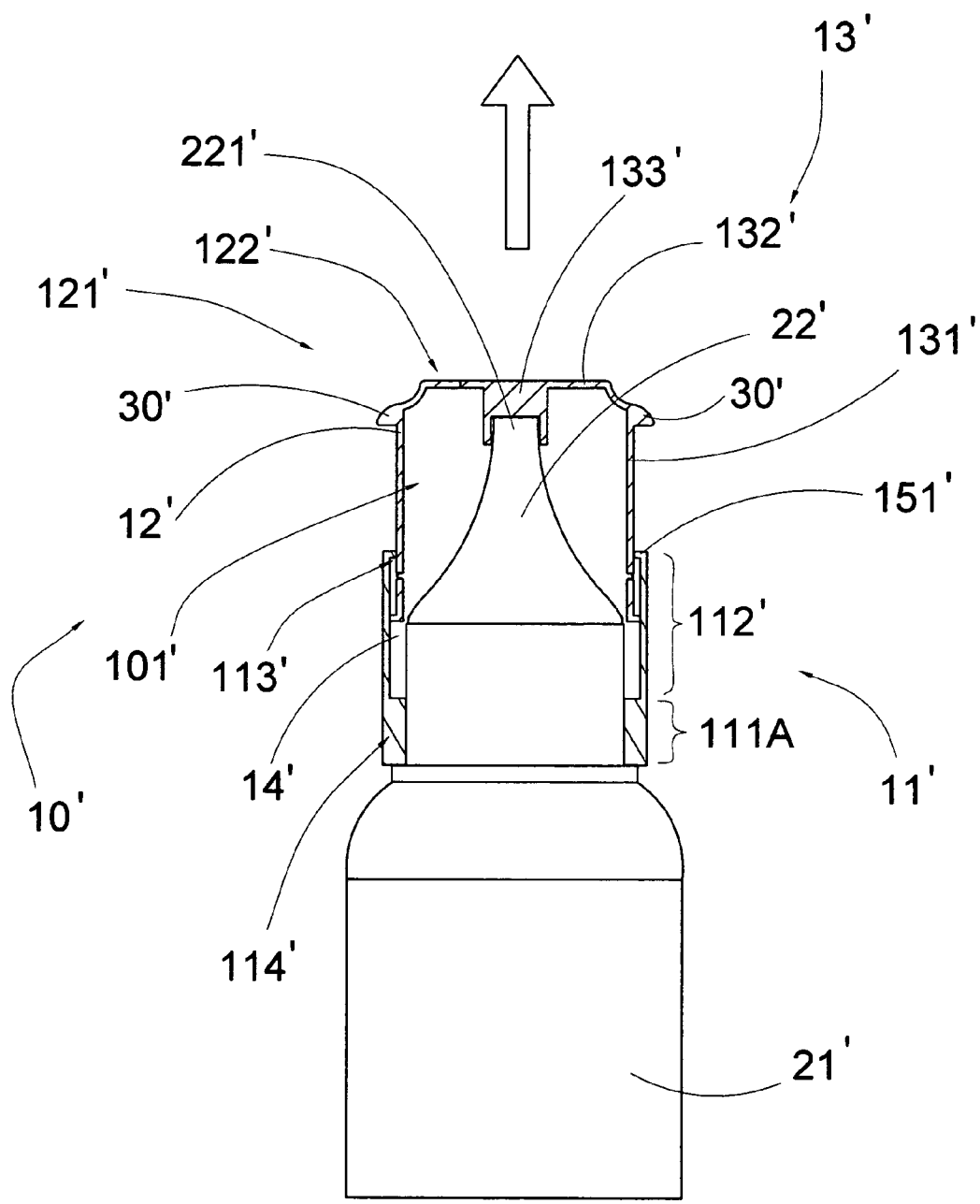
FIG. 14 illustrates an alternative mode of the dispenser cap according to the above second preferred embodiment of the present invention.

Alternatively, the lower ring portion 111A of the cap holder 11' can also be permanently affixed to the neck portion of the dispenser container 21', as shown in FIG. 14'. Therefore, the manufacturer can choose to permanently seal the cap holder 11' with the dispenser container 21' to prevent the dispenser cap 10' from being lost or reused by the user if it so desires.

According to the preferred embodiment, in order to instill the fluid to the eye of the user, the user simply needs to apply an upward pulling force at the eyelid-engaging member 12' and the cap enclosure 13' to lift up the guiding member 14', wherein the tip holder 133' will disengage from the tip 221' of the dispensing nozzle 22', as shown in FIG. 10. Once the bottom portions of eyelid-engaging member 12' and the cap enclosure 13' are slid out of the sliding cavity 113', the eyelid-engaging member 12' and the cap enclosure 13' will fold outwardly or "spring open" at the resilient joints 141' respectively to expose the dispensing nozzle 22', as shown in FIG. 11.

At its dispensing position, as shown in FIG. 13, the user places the container body 21' at the inverted position and uses the top side 121' of the eyelid-engaging member 12' to pull down or retract the lower eyelid to maintain the eyelid at the opened position. Accordingly, the tip 221' of the dispensing nozzle 22' will then align with the eye of the user so that when the user applies a squeezing force at the container body 21', a drop of fluid will flow through the tip 221' of the dispensing nozzle 22' and falls into the cul-de-sac or lower part of the eyeball.

Once the dispensing operation is completed, the user will then pivotally fold the cap enclosure 13' in to engage with the eyelid-engaging member 12' and simultaneously push both the eyelid-engaging member 12' and the cap enclosure 13' back down into the sliding cavity 113' until the tip holder 133' engages with the tip 221' of the dispensing nozzle 22'.

It is worth mentioning that the dispensing cap 10' not only serves as a sealing device like a conventional cap to enclose the dispensing nozzle 22' at the storage position but also forms an eyelid-engaging member to maintain the eyelid of the user in an opened position and to help aligning the dispensing nozzle 22' to the eye of the user. Through the engaging structure at the bottom of the cap holder 11', the dispenser cap 10' can be an universal cap made to apply on any type of container bodies 21' having an outer threaded portion. In other words, the dispenser cap 10' does not require altering the original structural design of the container body 21', so as to minimize the manufacturing cost of the eye-drop container intended to incorporate with the dispenser cap 10'. In addition, the hand and eye of the user will less likely touch the dispensing nozzle 22' throughout the operation of dispenser and the contamination of the fluid will be minimized as well.

Figure 15:
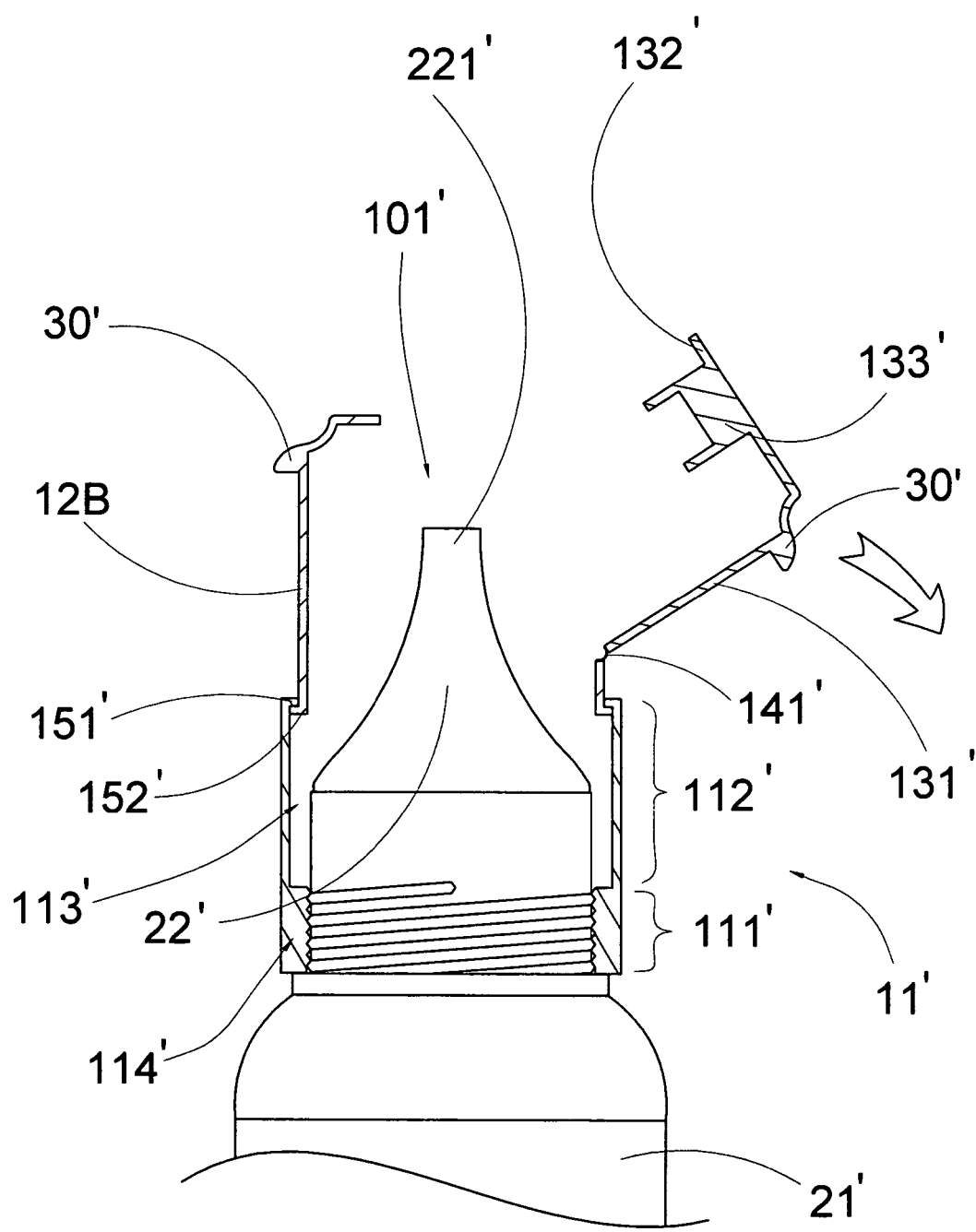
FIG. 15 illustrates a second alternative mode of the dispenser cap according to the above second preferred embodiment of the present invention.

FIG. 15 illustrates another alternative mode of the dispenser cap 10'. Accordingly, the cap enclosure 13' is extended upwardly from the cap holder 11' and has one end foldably extended with respect to the cap holder 11' in a pivotal manner. The modification of this alternative mode is that the eyelid-engaging member 12B is made as a single piece without the resilient joint so that in this case, it can only move upward and extends from the cap holder 11' in a non-pivotal manner. The cap enclosure 13' will continue to either open up to form the dispensing position or fold close to create a storage position. In other words, the eyelid-engaging member 12B can be made as a single piece support without any bendable part while the cap enclosure 13' can either fold towards the eyelid-engaging member 12B to enclose the tip 221' of the dispensing nozzle 22' or fold away from the eyelid-engaging member 12B to expose the tip 221' of the dispensing nozzle 22'.

Another possibility of this modification is that the eyelid-engaging member 12B is simply an extension of cap holder 11'. It will not contain any moving part or resilient joint but simply made as a rigid extension from the cap holder 11'. The only part that moves with this design is the cap enclosure 13'. It will continue to either fold towards the eyelid-engaging member 12B to enclose the tip 221' of the dispensing nozzle 22' or fold away from the eyelid-engaging member 12B to expose the tip 221' of the dispensing nozzle 22'.

Figure 16:
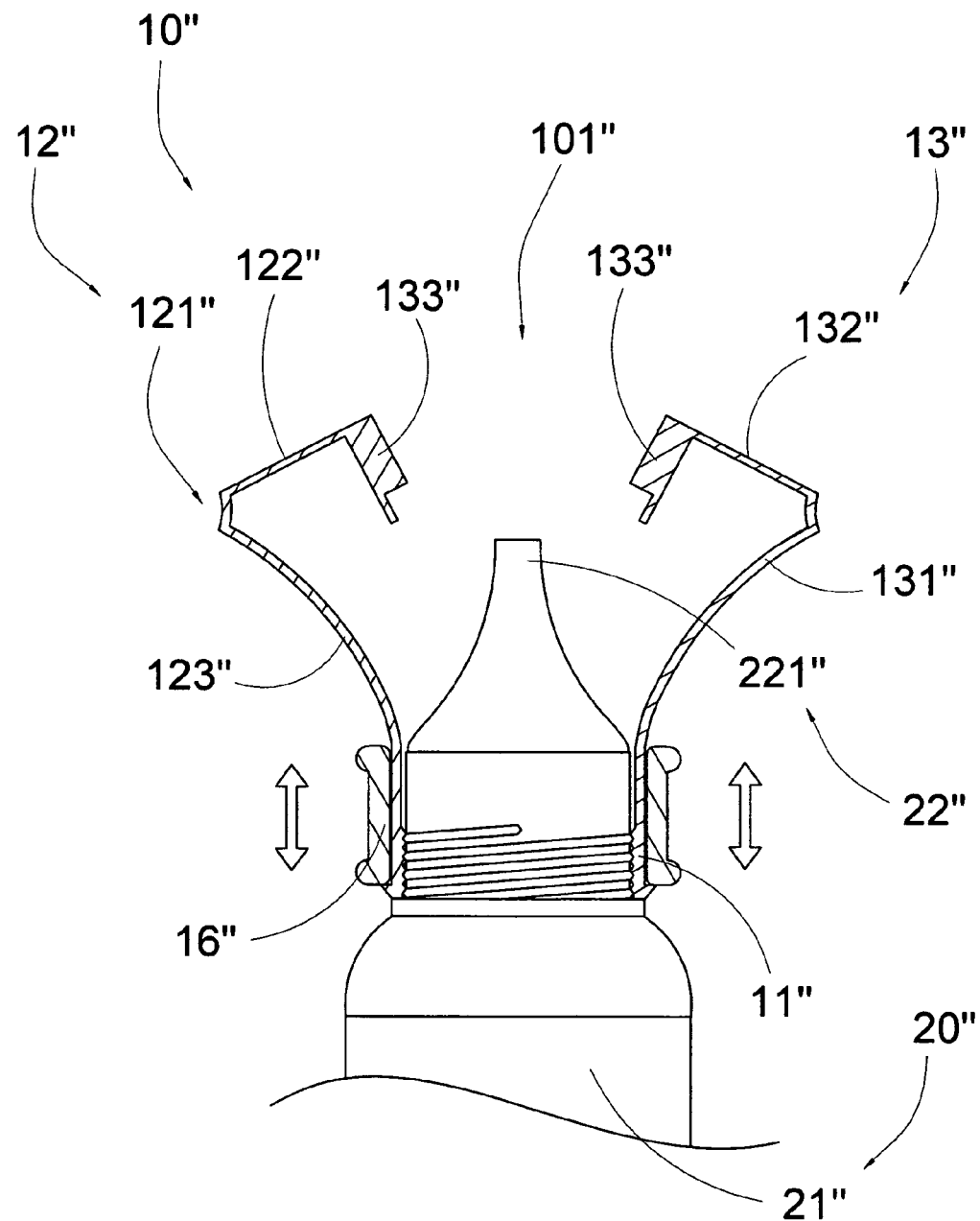
FIG. 16 is a cross-sectional view of the dispenser cap for the eye-drop container according to a third preferred embodiment of the present invention.

As shown in FIG. 16, an eye-drop container of a second preferred embodiment illustrates an alternative mode of the first embodiment of the present invention, wherein the eye-drop container comprises a dispenser cap 10" and a dispenser container 20" being closed by the dispenser cap 10".

The dispenser container 20" comprises a container body 21" for storing the fluid, such as ophthalmic drops, and a dispensing nozzle 22" upwardly extended from the neck portion of the container body 21" to dispense the fluid when the container body 21" is in an inverted or tilted position. Preferably, the container body 21" is made of squeezable material such that the user is able to squeeze the container body 21" to dispense the drops from the tip 221" of the dispensing nozzle 22".

The dispenser cap 10" comprises a cap holder 11" for detachably engaging with the container body 21", and an enclosure guider coupling with the cap holder 11". The enclosure guider comprises an eyelid-engaging member 12" upwardly extended from the cap holder 11", and a cap enclosure 13" upwardly extended from the cap holder 11" at a position opposite the eyelid-engaging member 12".

Accordingly, the eyelid-engaging member 12" has a retracting sidewall 123" integrally and upwardly extended from the cap holder 11" and a top side 121" extended above the tip 221" of the dispensing nozzle 22". The eyelid-engaging member 12", having an L-shaped cross section, will also have an enlarged retracting surface 122" located on the top side 121" and a truncated outer rim. The top retracting surface 122" can be either a smooth surface or a surface with fine grooves, with both a concave inner and a convex outer edge (not shown in drawings) that conform to the contour of the eyelid and globe of the user. Therefore, the eyelid-engaging member 12" is used as an eyelid retractor to maintain the eyelids of the user in an opened position and the truncated edge of the eyelid-engaging member 12" will facilitate the alignment of the bottle to the eye.

The cap enclosure 13" is integrally and upwardly extended from the cap holder 11" to either open up to form a dispensing position or fold close to create a storage position. The cap enclosure 13" comprises an enclosing sidewall 131", integrally extended from the cap holder 11" with an enclosing ceiling 132", which transversely extends from the enclosing sidewall 131" at a position slightly above the tip 221" of the dispensing nozzle 22" to form a tight seal at the tip 221" when the cap is in the storage position.

As shown in FIG. 16, both the retracting sidewall 123" of the eyelid-engaging member 12" and the enclosing sidewall 131" of the cap enclosure 13" are made of elastic or flexible material and are naturally formed in curved shape so that the retracting sidewall 123" of the eyelid-engaging member 12" and the enclosing sidewall 131" of the cap enclosure 13" are bent outwardly. Therefore, at the dispensing position, the cap enclosure 13" is outwardly folded apart from the eyelid-engaging member 12" to expose the tip 221" of the dispensing nozzle 22"; and at the storage position, the cap enclosure 13" is folded close or "pinched together" with the eyelid-engaging member 12" to form a nozzle cavity 101" within the two pieces for enclosing the dispensing nozzle 22".

The enclosure guider further comprises an actuating ring 16" slidably coupling around the retracting sidewall 123" of the eyelid-engaging member 12" and the enclosing sidewall 131" of the cap enclosure 13" to control the eyelid-engaging member 12" and the cap enclosure 13" between the dispensing position and the storage position. Accordingly, when the actuating ring 16" is pushed downward towards the cap holder 11", the eyelid-engaging member 12" and the cap enclosure 13" will bent outward to expose the tip 221" of the dispensing nozzle 22" because of the flexible characteristic of the retracting sidewall 123" of the eyelid-engaging member 12" and the enclosing sidewall 131" of the cap enclosure 13". And conversely, when the actuating ring 16" is pulled upward, the eyelid-engaging member 12" and the cap enclosure 13" are forced to fold close for enclosing the dispensing nozzle 22".

One half portion of the tip holder 133" is extended from the underside of the cap enclosure's top 132" while the other half portion of the tip holder 113" is extended from the underside of the top side of the eyelid-engaging member 12". Therefore, when the eyelid-engaging member 12" is folded close or "pinched together" with the cap enclosure 13", the tip 221" of the dispensing nozzle 22" will be enclosed or sealed by the two half portions of the tip holder 133" to prevent accidental spillage or contamination of the fluid.

In order to instill the fluid into the eye of the user, the user simply needs to apply a downward pushing force at the actuating ring 16" to lower the actuating ring 16". Once the actuating ring 16" is slid downwardly, the eyelid-engaging member 12" and the cap enclosure 13" will "flex" outward or "spring open" by their flexible characteristic to expose the dispensing nozzle 22".

Once the dispensing operation is completed, the user will then apply an upward pulling force at the actuating ring 16" to lift up the actuating ring 16" which in turn will simultaneously push both the eyelid-engaging member 12" and the cap enclosure 13" toward each other for enclosing the dispensing nozzle 22". It is worth mentioning that throughout the operation of the dispenser cap 10", only the actuating ring 16" will be involved to move the dispenser cap 10" between the dispensing position and the storage position. In other words, the user will no longer need to touch the eyelid-engaging member 12" and the cap enclosure 13" throughout the operation of the dispenser cap 10", and potential contamination of the dispensing nozzle 22' can further be minimized.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed:

1. A dispenser cap for an eye-drop container having a dispensing nozzle, which comprises:
    a cap holder adapted for securely coupling with said eye-drop container; and
    an enclosure guider, which comprises:
    an eyelid-engaging member upwardly and foldably extended with respect to said cap holder, wherein said eyelid-engaging member has a top side extended above a tip of said dispensing nozzle of said eye-drop container for contacting with the lower eyelid of a user to maintain said lower eyelid in an opened position in such a manner that when said eye-drop container is in an inverted position, said eyelid-engaging member is adapted for pulling down said lower eyelid, maintaining said eyelid in said opened position, and directly aligning said dispensing nozzle with said user's eye to dispense fluid from said eye-drop container; and
    a cap enclosure upwardly and foldably extended with respect to said cap holder and alongside said eyelid-engaging member, wherein said cap enclosure is adapted to fold between a dispensing position and a storage position, wherein in the dispensing position, said eyelid-engaging member and said cap enclosure are outwardly folded to expose said dispensing nozzle, and in said storage position, said cap enclosure is folded in to engage with said eyelid-engaging member to form a nozzle cavity within both said eyelid-engaging member and said cap enclosure to enclose said dispensing nozzle within said nozzle cavity.

2. The dispenser cap, as recited in claim 1, wherein said eyelid-engaging member has an L-shaped cross section and an enlarged top surface, said L-shaped cross section and enlarged top engaging surface defining the top side eyelid-engaging member for engaging with the lower eyelid of the user.

3. The dispenser cap, as recited in claim 2, wherein said eyelid-engaging member has a concave inner edge and a convex outer edge, conforming to a contour of said eyelid and globe of said user to pull down said eyelid and to maintain said eyelid in said opened position.

4. The dispenser cap, as recited in claim 3, wherein said cap enclosure comprises an enclosing sidewall foldably extended from said cap holder and an enclosing ceiling transversely extended from said enclosing sidewall at a position slightly above the tip of said dispensing nozzle that when said cap enclosure is folded in to meet with the top side of said eyelid-engaging member edge-to-edge, said nozzle cavity is created to enclose the dispensing nozzle.

5. The dispenser cap, as recited in claim 4, wherein said cap enclosure further comprises a tip holder downwardly extended from an underside of said enclosing ceiling for encirclingly sealing said dispensing nozzle tip when said cap enclosure is folded in to engage with said eyelid-engaging member.

6. The dispenser cap, as recited in claim 5, wherein said enclosure guider further comprises a guiding member slidably engaged with said cap holder and arranged in such a manner that when said guiding member is upwardly slid with respect to said cap holder, both said eyelid-engaging member and said cap enclosure are upwardly lifted and outwardly folded to expose said dispensing nozzle, and conversely when said guiding member is downwardly slid with respect to said cap holder, both said eyelid-engaging member and said cap enclosure are downwardly dropped and inwardly folded to enclose the dispensing nozzle.

7. The dispenser cap, as recited in claim 6, wherein said enclosure guider further comprises two resilient joints, wherein said eyelid-engaging member and said cap enclosure are foldably coupled with said guiding member via said resilient joints respectively, such that when said guiding member is upwardly lifted, said eyelid-engaging member and said cap enclosure are outwardly folded at said resilient joints respectively.

8. The dispenser cap, as recited in claim 7, wherein said cap holder distinctly has a lower ring portion with a smaller inner diameter and an upper ring portion with a larger inner diameter and defines a sliding cavity within said upper ring portion for said guiding member to slide vertically.

9. The dispenser cap, as recited in claim 8, wherein a height of said guiding member is shorter than a height of said sliding cavity such that when said guiding member is downwardly slid towards said lower ring portion of said cap holder, bottom portions of said eyelid-engaging member and said cap enclosure are slid within said sliding cavity to ensure said eyelid-engaging member and said cap enclosure being engaged for enclosing said dispensing nozzle.

10. The dispenser cap, as recited in claim 9, wherein said cap holder further has an inner threaded portion provided at an inner side of said lower ring portion of said cap holder for detachably engaging with a neck portion of said eye-drop container.

11. The dispenser cap, as recited in claim 8, wherein said cap holder further has an inner threaded portion provided at an inner side of said lower ring portion of said cap holder for detachably engaging with a neck portion of said eye-drop container.

12. The dispenser cap, as recited in claim 6, wherein said cap holder distinctly has a lower ring portion with a smaller inner diameter and an upper ring portion with a larger inner diameter and defines a sliding cavity within said upper ring portion for said guiding member to slide vertically.

13. The dispenser cap, as recited in claim 12, wherein a height of said guiding member is shorter than a height of said sliding cavity such that when said guiding member is downwardly slid towards said lower ring portion of said cap holder, bottom portions of said eyelid-engaging member and said cap enclosure are slid within said sliding cavity to ensure said eyelid-engaging member and said cap enclosure being engaged for enclosing said dispensing nozzle.

14. The dispenser cap, as recited in claim 12, wherein said cap holder further has an inner threaded portion provided at an inner side of said lower ring portion of said cap holder for detachably engaging with a neck portion of said eye-drop container.

15. The dispenser cap, as recited in claim 3, wherein said enclosure guider further comprises a guiding member slidably engaged with said cap holder and arranged in such a manner that when said guiding member is upwardly slid with respect to said cap holder, both said eyelid-engaging member and said cap enclosure are upwardly lifted and outwardly folded to expose said dispensing nozzle, and conversely when said guiding member is downwardly slid with respect to said cap holder, both said eyelid-engaging member and said cap enclosure are downwardly dropped and inwardly folded to enclose the dispensing nozzle.

16. The dispenser cap, as recited in claim 15, wherein said enclosure guider further comprises two resilient joints, wherein said eyelid-engaging member and said cap enclosure are foldably coupled with said guiding member via said resilient joints respectively, such that when said guiding member is upwardly lifted, said eyelid-engaging member and said cap enclosure are outwardly folded at said resilient joints respectively.

17. The dispenser cap, as recited in claim 1, wherein said cap enclosure comprises an enclosing sidewall foldably extended from said cap holder and an enclosing ceiling transversely extended from said enclosing sidewall at a position slightly above the tip of said dispensing nozzle that when said cap enclosure is folded in to meet with the top side of said eyelid-engaging member edge-to-edge, said nozzle cavity is created to enclose the dispensing nozzle.

18. The dispenser cap, as recited in claim 17, wherein said cap enclosure further comprises a tip holder downwardly extended from an underside of said enclosing ceiling for encirclingly sealing said dispensing nozzle tip when said cap enclosure is folded in to engage with said eyelid-engaging member.

19. The dispenser cap, as recited in claim 1, wherein said enclosure guider further comprises a guiding member slidably engaged with said cap holder and arranged in such a manner that when said guiding member is upwardly slid with respect to said cap holder, both said eyelid-engaging member and said cap enclosure are upwardly lifted and outwardly folded to expose said dispensing nozzle, and conversely when said guiding member is downwardly slid with respect to said cap holder, both said eyelid-engaging member and said cap enclosure are downwardly dropped and inwardly folded to enclose the dispensing nozzle.

20. The dispenser cap, as recited in claim 19, wherein said enclosure guider further comprises two resilient joints, wherein said eyelid-engaging member and said cap enclosure are foldably coupled with said guiding member via said resilient joints respectively, such that when said guiding member is upwardly lifted, the eyelid-engaging member and the cap enclosure are outwardly folded at said resilient joints respectively.

* * * * *